US010302536B2

(12) United States Patent
Shi et al.

(10) Patent No.: US 10,302,536 B2
(45) Date of Patent: May 28, 2019

(54) SYSTEM AND APPARATUS FOR ISOLATING OR ENRICHING AGENTS USING FLOATATION

(71) Applicant: DIAGNOLOGIX, LLC, San Diego, CA (US)

(72) Inventors: Guixin Shi, San Diego, CA (US); Michael Benchimol, San Diego, CA (US); Tyler Watson, San Diego, CA (US)

(73) Assignee: DIAGNOLOGIX, LLC, San Diego, CA (US)

( * ) Notice: Subject to any disclaimer, the term of this patent is extended or adjusted under 35 U.S.C. 154(b) by 34 days.

(21) Appl. No.: 15/309,413

(22) PCT Filed: May 8, 2015

(86) PCT No.: PCT/US2015/029950
§ 371 (c)(1),
(2) Date: Nov. 7, 2016

(87) PCT Pub. No.: WO2015/175344
PCT Pub. Date: Nov. 19, 2015

(65) Prior Publication Data

US 2017/0176305 A1 Jun. 22, 2017

Related U.S. Application Data

(60) Provisional application No. 61/991,502, filed on May 10, 2014.

(51) Int. Cl.

| | |
|---|---|
| ***G01N 33/536*** | (2006.01) |
| ***G01N 1/40*** | (2006.01) |

(Continued)

(52) U.S. Cl.
CPC ............ *G01N 1/4077* (2013.01); *B03D 1/14* (2013.01); *C12M 47/04* (2013.01);
(Continued)

(58) Field of Classification Search
None
See application file for complete search history.

(56) References Cited

U.S. PATENT DOCUMENTS 3,880,163 A * 4/1975 Ritterskamp ....... A61M 5/2033 604/136
4,053,282 A 10/1977 Hach et al.
(Continued)

FOREIGN PATENT DOCUMENTS

DE 3412217 A1 10/1985
EP 1073716 A2 2/2001
(Continued)

OTHER PUBLICATIONS

Berry et al., Dextran and albumin derivatised iron oxide nanoparticles: influence on fibroblasts in vitro. Biomaterials, 24(25)4551-4557, 2003.

(Continued)

*Primary Examiner* — Christopher L Chin
(74) *Attorney, Agent, or Firm* — Wilson Sonsini Goodrich & Rosati

(57) ABSTRACT

Systems and devices for the isolation of biological agents that are infused in a solution causing those agents to float. These systems and devices have numerous research, diagnostic, clinical, consumer, and other applications. An aspect of the disclosure provides for an apparatus for isolation or enrichment of biological agents from a sample comprising: a sample container comprising an inner volume to hold a sample and a plurality of micro bubbles, a tapered end and an open end, a plunger inserted into the open end and a tip (Continued)

of the tapered end forming an acute angle relative to the horizontal axis of the sample container, wherein the plurality of micro bubbles float one or more biological agents of the sample and wherein the plunger moves towards the tip to isolate or enrich the one or more biological agents from the sample.

17 Claims, 17 Drawing Sheets

(51) Int. Cl.
*B03D 1/14* (2006.01)
*C12M 1/00* (2006.01)

(52) U.S. Cl.
CPC ..... *G01N 33/536* (2013.01); *B03D 2203/003* (2013.01); *G01N 2001/4066* (2013.01)

(56) References Cited

U.S. PATENT DOCUMENTS

| | | | | | |
|---|---|---|---|---|---|
| 4,135,510 | A * | 1/1979 | Assouly | A61M 5/3134 604/218 |
| 4,138,474 | A * | 2/1979 | Updike | G01N 33/538 210/504 |
| 4,316,391 | A * | 2/1982 | Tickner | A61B 8/06 424/9.52 |
| 4,655,749 | A * | 4/1987 | Fischione | A61M 25/10184 600/561 |
| 4,751,921 | A * | 6/1988 | Park | A61B 17/8827 604/190 |
| 4,902,429 | A | 2/1990 | Carpenter et al. | |
| 5,116,724 | A | 5/1992 | Delaage et al. | |
| 6,135,984 | A * | 10/2000 | Dishler | A61F 9/007 604/181 |
| 6,139,819 | A | 10/2000 | Unger et al. | |
| 6,177,061 | B1 * | 1/2001 | Klaveness | A61K 49/223 424/9.51 |
| 6,245,318 | B1 | 6/2001 | Klibanov et al. | |
| 6,261,537 | B1 | 7/2001 | Klaveness et al. | |
| 6,806,045 | B2 | 10/2004 | Kulseth et al. | |
| 6,936,053 | B1 | 8/2005 | Weiss et al. | |
| 8,460,269 | B2 | 6/2013 | Toma et al. | |
| 8,513,032 | B2 | 8/2013 | Jablonski et al. | |
| 8,835,186 | B2 | 9/2014 | Jablonski et al. | |
| 2003/0104359 | A1 | 6/2003 | Cuthbertson et al. | |
| 2005/0260189 | A1 | 11/2005 | Klibanov et al. | |
| 2007/0036722 | A1 | 2/2007 | Rongved et al. | |
| 2008/0166786 | A1 | 7/2008 | Nishiyama | |
| 2009/0176201 | A1 | 7/2009 | Jablonski et al. | |
| 2010/0181234 | A1 | 7/2010 | Clayton et al. | |
| 2011/0236884 | A1 | 9/2011 | Jablonski et al. | |
| 2011/0251485 | A1 * | 10/2011 | Horton | A61M 5/1452 600/432 |
| 2012/0244078 | A1 | 9/2012 | Rychak | |
| 2012/0288852 | A1 | 11/2012 | Willson et al. | |
| 2014/0142468 | A1 | 5/2014 | Hossack et al. | |
| 2015/0219636 | A1 | 8/2015 | Rychak | |
| 2016/0167061 | A1 | 6/2016 | McNaughton et al. | |

FOREIGN PATENT DOCUMENTS

| | | |
|---|---|---|
| WO | WO-99/55837 | 11/1999 |
| WO | WO-2009052057 A1 | 4/2009 |
| WO | WO-2015175344 A1 | 11/2015 |

OTHER PUBLICATIONS

Brown et al., Foam fractionation of globular proteins. Biotechnology and Bioengineering, 36:947-959, 1990.
Burapatana et al., A comparison of the activity reduction occurring in two detergent-assisted protein (Cellulase and Lysozyme) foam fractionation processes. Separation Science and Technology, 40(12):2445-2461, 2005.
Burapatana et al., Effect of buffer and pH on detergent-assisted foam fractionation of cellulase. Ind. Eng. Chem. Res., 44:4968-4972, 2005.
Crofcheck and Gillette, Evaluation of foam fractionation column scale-up for recovering bovine serum albumin. Transactions of the ASEA, 46(6):1759-1764, 2003.
Faraji and Wipf, Nanoparticles in cellular drug delivery, Bioorganic & Medicinal Chemistry, 17(8)2950-2962, 2009.
Hus et al., Isolating cells from blood using buoyancy activated cell sorting (BAGS) with glass microbubbles. 14th International Conference on Miniaturized Systems for Chemistry and Life Sciences. Oct. 3-7, 2010, Groningen, The Netherlands, p. 226-228.
Jeong and Corapcioglu, A micromodel analysis of factors influencing NAPL removal by surfactant foam flooding. Journal of Contaminant Hydrology, 60:77-96, 2003.
Jeong and Corapcioglu, Physical model analysis of foam-TCE displacement ion porous media. Environmental and energy Engineering, 49(3):782-788, 2003.
Maruyama et al., Batch foam separation of a soluble protein. Water Research, 41:710-718, 2007.
Moore et al., Uptake of dextran-coated monocrystalline iron oxides in tumor cells and macrophages. Journal of Magnetic Resonance Imaging, 7(6):140-1145,1997.
PCT Patent Application No. PCT/US2015/29950 International Search Report and Written Opinion dated Jul. 24, 2015.
Pisanic et al., Nanotoxicity of iron oxide nanoparticle internalization in growing neurons. Biomaterials, 28(16):2572-2581, 2007.
Rychak et al., Deformable gas-filled microbubbles targeted to P-selectin. J Control Release. 14(3):288-99, 2006.
Saleh and Hossain, A study of the separation of proteins from multicomponent mixtures by a semi-batch foaming process. Chemical Engineering and Processing, 40:371-378, 2001.
Shi et al., Binding and isolation of tumor cells in biological media with perfluorocarbon microbubbles. Methods. 64(2):102-7, 2013.
Shi et al., Isolation of rare tumor cells from blood cells with buoyant immuno-microbubbles. PLoS One. 8(3):e58017, 2013.
Simberg et al., Targeting of perfluorocarbon microbubbles to selective populations of circulating blood cells. J Drug Target. 17(5):392-8, 2009.
PCT/US2015/029950 International Preliminary Report on Patentability dated Nov. 24, 2016.
European Patent Application No. EP 15793428.2 extended European Search Report dated Dec. 22, 2017.

* cited by examiner

| Cell Viability after high ambient pressure treatment | | |
|---|---|---|
| Time (min)/Group | Control group | Pressure-treated group |
| 0 | 99.1% | 99.2% |
| 30 | 97.7% | 97.7% |
| 120 | 97.7% | 97.5% |

SYSTEM AND APPARATUS FOR ISOLATING OR ENRICHING AGENTS USING FLOATATION

CROSS-REFERENCE TO RELATED APPLICATIONS

This application is filed pursuant to 35 U.S.C. § 371 as a United States National Phase Application of International Application No. PCT/US2015/029950 filed May 8, 2015, which claims the benefit of U.S. Provisional Application No. 61/991,502, filed on May 10, 2014, each of which are incorporated herein by reference in their entireties.

STATEMENT REGARDING FEDERALLY SPONSORED RESEARCH

This invention was made with government support under 1R43CA176892-01A1, 3R43CA176892-01A1S1, 1R43HL126285-01, and 2R44CA176892 awarded by the National Institutes of Health. The government has certain rights in the invention.

BACKGROUND OF THE INVENTION

There is an unmet need for cost-efficient technologies for high-purity isolation and analysis of cells in animal blood and tissue solutions. The prior art describes several methods for isolating these cells through centrifugation and through the application of magnetic force. Other methods of cell isolation also include use of microfluidics, filtration, and others.

Centrifugation, the use of centrifugal force for the sedimentation of heterogeneous mixtures with a centrifuge, is a common method for isolating cells in animal blood. The prior art describes a number of centrifuge apparati, but these apparati are expensive and complex, such that, primarily, only laboratories can afford them, and only laboratory technicians can operate them. This limits the clinical and consumer applications of centrifugal isolation. Furthermore, centrifugation-based methods separate cells based on physical properties (e.g. density, size, shape), and do little to separate cell based on protein expression and biochemical profile.

Magnetic force is an alternative to centrifugal force for isolating cells in animal blood. An example of this application from the prior art is the use of immunomagnetic nanobeads and lateral magnetophoresis for isolation of circulating tumor cells (CTC's). While effective, the application of this isolation method is costly and requires the expertise of a laboratory-trained technician. This limits the clinical and consumer applications of magnetic force isolation.

Centrifugal and magnetic force isolation of cells in animal blood entails infusing the cells in a solution causing them to fall. An innovation is to use microbubbles with selection markers adjacent thereto for cell isolation. Microbubbles are bubbles less than can be less than a millimeter in diameter to greater than a micrometer in diameter. Microbubbles can be filled inside with a gas, such as air or perfluorocarbon. Adjacent to cells or other biological agents or non-biological agents, microbubbles can cause those agents to float in a liquid. In some instances, biological or non-biological agents can float in the presence or absence of microbubbles adjacent thereto by including a liquid or gas, or combination thereof, that cause the agents to float, such as solutions that are known in the art. In some instances, the microbubbles, adjacent thereto biological agents or non-biological agents that are isolated or enriched, are disrupted.

Generally, cells with microbubble adjacent thereto are placed into standard centrifuge tubes for the application of centrifugal or magnetic force for isolation or enrichment. The prior art uses certain inverted tubes and other container apparati to increase microbubble effectiveness, but none of these apparati allow for the isolation of cells absent a centrifugal force, and a laboratory-trained technician to properly apply this force to the agents. This creates high costs and inefficient isolation results.

These high costs and inefficient results limit the application of the prior art's isolation methods. Large research institutions, along with well-funded private companies, can afford to apply these isolation methods, but smaller entities or personal or consumer users and clinics lacking laboratory equipment and know-how, cannot. Furthermore, the prior art has no practically implementable consumer applications, as ordinary consumers lack the level of skill needed to operate a centrifuge or a magnetic force application, and the resources needed to purchase expensive equipment.

While the prior art illustrates methods and devices for improving existing cell isolation techniques, it provides no viable alternative for isolating cells, whether microbubble-adjacent thereto or not, without the application of centrifugal or magnetic force, and the necessary laboratory expenses and know-how to apply such forces. Life-saving applications of isolating cells from animal blood, in clinical and consumer environments, are limited as a result.

Cells from animal blood are not the only biological agents isolated through centrifugal and magnetic force technology. Other potentially life-saving applications include the isolation of cells (such as stem cells, immune cells, circulating tumor cell cells (CTC's), tumor cells, or other cells), cell fragments, bacteria, viruses, parasites, and others. The development of alternatives to centrifugal and magnetic force for isolating biological agents is critical in order to apply the life-saving properties of those isolated biological agents to the home and to the clinic.

SUMMARY OF THE INVENTION

An aspect of the disclosure provides for an apparatus for isolation or enrichment of biological agents from a sample comprising: a sample container comprising an inner volume to hold a sample and a plurality of microbubbles, a tapered end and an open end, a plunger inserted into the open end and a tip of the tapered end forming an acute angle relative to the horizontal axis of the sample container, wherein the plurality of microbubbles float one or more biological agents of the sample and wherein the plunger moves towards the tip to isolate or enrich the one or more biological agents from the sample.

In some instances, the acute angle is between about 5 degrees and about 40 degrees. In some instances, the acute angle is between about 5 degrees and about 10 degrees. In some instances, the acute angle is about 35 degrees.

In some instances, the apparatus comprises a container spout directionally orienting one or more droplets that form from the tip comprising the one or more biological agents. In some instances, the apparatus comprises a collection container to collect the one or more droplets. In some instances, the collection container is adjacent to the outer surface of the sample container. In some instances, the collection container is mounted onto the outer surface of the sample container close to the bottom end of the container spout.

Another aspect of the disclosure provides for an apparatus for isolation or enrichment of biological agents from a sample comprising: a sample container comprising an inner volume to hold a sample and a plurality of microbubbles, a tapered end and an open end, a plunger inserted into the open end, and a tip of the tapered end perpendicular relative to the horizontal axis of the sample container, wherein the plurality of microbubbles float one or more biological agents of the sample and wherein the plunger moves towards the tip to isolate or enrich the one or more biological agents from the sample. In some instances, the plunger is operated manually by a user.

In some instances, the apparatus comprises a drive screw mechanically coupled to the plunger, wherein rotation of the drive screw is mechanically converted to linear translation of the plunger. In some instances, the apparatus comprises a container mount to house the drive screw. In some instances, a bottom flange of the sample container is secured to the container mount by inserting the bottom flange into a locking flange slot on the container mount. In some instances, the drive screw is operated manually by a user. In some instances, the drive screw is operated automatically by a drive motor. In some instances, the drive screw is operated automatically by a drive motor remotely controlled by a microprocessor. In some instances, the apparatus comprises an apparatus enclosure to house the drive motor.

In some instances, the apparatus comprises a plunger adapter joint and a plunger engagement adapter, wherein the plunger adapter joint is adjacent to the plunger and the plunger engagement adapter, and the plunger engagement adapter is adjacent to the plunger adapter joint and the drive screw. In some instances, the container mount comprises a sensor depressor and sensor mount. In some instances, the container mount further comprises a wire port. In some instances, the container mount further comprises a screw port.

In some instances, the sample container is formed of a material to provide the inner volume of the sample container hydrophilicity. In some instances, the sample container is formed of a material to provide the inner volume of the sample container hydrophobicity. In some instances, the material is glass. In some instances, a hydrophilic layer is adjacent thereto the inner volume of the sample container. In some instances, a hydrophobic layer is adjacent thereto the tapered end of the inner volume of the sample container. In some instances, a hydrophilic layer is adjacent thereto the inner volume of the sample container and a hydrophobic layer is adjacent thereto the tapered end of the inner volume. In some instances, the sample container is formed of a material to provide hydrophilicity to the inner volume and a hydrophobic layer is adjacent thereto the tapered end of the inner volume. In some instances, the hydrophilic layer is bovine serum albumin. In some instances, the hydrophobic layer is SURFASIL™. In some instances, the hydrophobic layer is paraffin, polytetrafluoroethylene, poloaxmer, or combinations thereof.

In some instances, the sample container holds a sample volume of between about 1 mL and about 10 mL. In some instances, the sample container holds a sample volume of between about 10 mL and about 50 mL. In some instances, the sample container holds a sample volume of between about 50 mL and about 200 mL. In some instances, the sample is diluted.

In some instances, the sample is tissue, blood, bone marrow, urine, saliva, cerebrospinal fluid, seminal fluid, sputum, stool, joint fluid, lymph, amniotic fluid, bile, ascites, or pleural effusion, or combinations thereof. In some instances, the sample is umbilical cord blood. In some instances, the sample is circulating blood. In some instances, the sample is tumor tissue. In some instances, the sample is fluid within and surrounding a tumor tissue. In some instances, the biological agents are cells. In some instances, the cells are circulating tumor cells (CTCs). In some instances, the cells are bone marrow cells. In some instances, the cells are fetal cells from a mother's blood.

In some instances, a ratio of the cells to the plurality of microbubbles is about 1:100. In some instances, a ratio of the cells to the plurality of microbubbles is about 1:500. In some instances, a ratio of the cells to the plurality of microbubbles is about 1:1000.

In some instances, the biological agents isolated or enriched are less than 0.5% of the total sample. In some instances, the biological agents isolated or enriched are less than 0.1% of the total sample. In some instances, the biological agents isolated or enriched are less than 0.01% of the total sample. In some instances, the biological agents isolated or enriched are less than 0.001% of the total sample.

In some instances, the microbubbles are lipid shell microbubbles, albumin shell microbubbles, polymer shell microbubbles, lipopolymer shell microbubbles or glass microbubbles, or combinations thereof. In some instances, the shell of each microbubble comprises lipid, protein, polymer, lipopolymer, or glass or combinations thereof.

In some instances, the plurality of microbubbles have an outer diameter of between about 1 micron and about 10 microns. In some instances, the plurality of microbubbles have an outer diameter of between about 2 microns and about 8 microns. In some instances, the plurality of microbubbles have an outer diameter of between about 2 microns and about 20 microns.

In some instances, a plurality of selection markers are adjacent to the outer surface of the plurality of microbubbles. In some instances, the plurality of selection markers bind the outer surface by nucleophilic conjugate addition. In some instances, the plurality of selection markers bind the outer surface by Michael addition. In some instances, the plurality of selection markers per microbubble is between about 200,000 and about 500,000. In some instances, a surface density of the plurality of selection markers adjacent to the outer surface of a single microbubble of the plurality of microbubbles is between about 3,000 and about 6,000 selection markers per square micron. In some instances, a surface density of the plurality of selection markers adjacent to the outer surface of a single microbubble of the plurality of microbubbles is between about 1,000 and about 3,000 selection markers per square micron. In some instances, a surface density of the plurality of selection markers adjacent to the outer surface of a single microbubble of the plurality of microbubbles is less than about 6,000 selection markers per square micron. In some instances, a surface density of the plurality of selection markers adjacent to the outer surface of a single microbubble of the plurality of microbubbles is less than about 3,000 selection markers per square micron. In some instances, the plurality of selection markers per microbubble is between about 300,000 and about 400,000.

In some instances, the plurality of selection markers comprise a first set and a second set. In some instances, each of the plurality of microbubbles comprise the first set and the second set of selection markers. In some instances, a first set of the plurality of microbubbles comprise the first set of selection markers and a second set of the plurality of microbubbles comprise the second set of selection markers.

In some instances, cells attach the plurality of microbubbles by receptor ligand interactions. In some instances, one or more selection markers bind cell surface markers. In some instances, one or more selection markers are different. In some instances, one or more selection markers are antibodies. In some instances, one or more selection markers are molecules that bind tumor markers. In some instances, one or more selection markers are molecules that bind stem cell markers. In some instances, one or more selection markers are molecules that bind cell surface marker, EpCAM. In some instances, one or more selection markers are molecules that bind cell surface marker, CD133. In some instances, one or more selection markers are molecules that bind cell surface marker, CD34.

In some instances, at least about 80% of the cells bind at least one of the plurality of microbubbles. In some instances, at least about 85% of the cells bind at least one of the plurality of microbubbles. In some instances, at least about 90% of the cells bind at least one of the plurality of microbubbles. In some instances, at least about 95% of the cells bind at least one of the plurality of microbubbles.

In some instances, a biological agent of the sample floats when at least about 2 microbubbles are adjacent thereto. In some instances, a biological agent of the sample floats when at least about 3 microbubbles are adjacent thereto. In some instances, a biological agent of the sample floats when between about 2 to about 20 microbubbles are adjacent thereto.

In some instances, the apparatus is compatible with downstream assays. In some instances, the downstream assays comprise cell staining, molecular analysis, or cell culture, or combinations thereof.

In some instances, the apparatus is sterile. In some instances, the apparatus comprises a sterile liquid in the inner volume to enhance viability of the sample. In some instances, the apparatus comprises a sterile liquid in the inner volume to cause the plurality of microbubbles to float. In some instances, the density of the liquid is between about 0.9 and about 1.1 grams per cubic centimeter.

In some instances, the apparatus is used in a clinical or laboratory setting. In some instances, the apparatus is used in a residential setting. In some instances, the apparatus is utilized for personal use.

In some instances, the apparatus comprises a bottom stop sensor, a stepper motor, a top drip detector, a power supply, a microcontroller board, or combinations thereof.

Another aspect of the disclosure provides for a method for isolation or enrichment of biological agents from a sample comprising (a) obtaining a sample and a plurality of microbubbles, (b) adding the sample and the plurality of microbubbles to an inner volume of a sample container, (c) orienting the tapered end of the sample container away from ground wherein the plurality of microbubbles float one or more biological agents towards a tip of the tapered end, and (d) moving a plunger from an open end of the sample container towards the tapered end to isolate or enrich one or more biological agents from the sample.

In some instances, the method comprises disrupting the plurality of microbubbles after (d). In some instances, ambient pressure is increased to disrupt the plurality of microbubbles. In some instances, ambient pressure is increased to between about 2 atm and about 4 atm for between about 2 minutes and about 10 minutes to disrupt the plurality of microbubbles. In some instances, ambient pressure is increased to about 3 atm for about 5 minutes to disrupt the plurality of microbubbles.

In some instances, the method comprises incubating the plurality of microbubbles and the sample in the inner volume for at least about 1 minute before (c) or (d). In some instances, the method comprises incubating the plurality of microbubbles and the sample in the inner volume for at least about 5 minutes before (c) or (d). In some instances, the method comprises incubating the plurality of microbubbles and the sample in the inner volume for at least about 10 minutes before (c) or (d). In some instances, the method comprises sterilizing the inner volume of the sample container prior to adding of (b).

Another aspect of the disclosure provides for a kit for isolation or enrichment of biological agents from a sample comprising one or more sample containers, an apparatus enclosure, a container mounts, one or more selection markers, components to form microbubbles, instructions for forming microbubbles, and instructions for using the sample container.

Another aspect of the disclosure provides for a kit for isolation or enrichment of biological agents from a sample comprising one or more sample containers, an apparatus enclosure, a container mount, microbubbles with one or more selection markers adjacent thereto, and instructions for using the sample container.

Another aspect of the disclosure provides for a kit for isolation or enrichment of biological agents from a sample comprising one or more sample containers, one or more selection markers, components to form microbubbles, instructions for forming microbubbles, and instructions for using the sample container.

In some instances, the apparatus is used in a remote geographical area. In some instances, the apparatus is used in an impoverished or low-income area. In some instances, the apparatus is used in the absence of sterilization equipment. In some instances, the apparatus is used in the absence of centrifugation equipment. In some instances, the apparatus is used by a clinician. In some instances, the apparatus is used by a researcher. In some instances, the apparatus is used by a lay person. In some instances, the apparatus is used by a consumer. In some instances, the apparatus is used for cord blood banking. In some instances, the apparatus is used for isolation of immune cells for immunotherapy in cancer treatment. In some instances, the apparatus is used for isolation of hematopoietic stem cells from umbilical cord blood following a live birth. In some instances, the apparatus is used for isolation of one or more narcotics from a blood sample or urine sample. In some instances, the apparatus is used for depletion of one or more biological agents from a sample. In some instances, the apparatus is used for depletion of one or more non-biological agents from a sample.

Another aspect of the disclosure provides for an apparatus for isolation or enrichment of agents from a sample comprising: a sample container comprising an inner volume to hold a sample and a liquid, a tapered end and an open end, a plunger inserted into said open end, and a tip of said tapered end forming an acute angle relative to the horizontal axis of said sample container, wherein said liquid floats one or more agents of said sample and wherein said plunger moves towards said tip to isolate or enrich said one or more agents from said sample.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION OF THE INVENTION

Figure 1A:
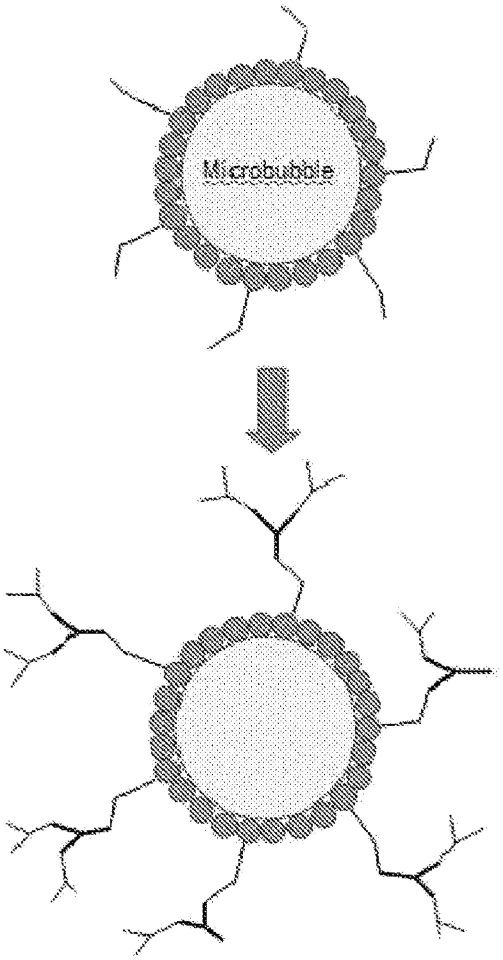
FIG. 1A illustrates synthesis of microbubbles that are adjacent thereto cells, FIG. 1B.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

This present disclosure comprises a sterilized sample container apparatus, existing as part of an open or closed system. The apparatus can isolate biological including animal cells, animal cell fragments, bacteria, viruses, fungi, parasites, plant cells, or non-biological agents including chemical agents, industrial agents, agricultural agents, and other biological or non-biological agents.

The present disclosure can comprise mechanisms to keep the apparatus sterile, plunging systems, collection containers for isolating biological agents, hydrophobic materials, hydrophilic materials, non-specific interaction blocking agents, syringe needle systems, sterile syringes, infusion needles, or liquids or combinations thereof.

The present disclosure may be applied to a number of applications including clinical, research, diagnostic, industrial, institutional, or consumer, or uses or combinations thereof. In some instances, the present disclosure is used for the isolation or enrichment of biological or non-biological agents. In some instances, the present disclosure is used from the depletion of biological or non-biological agents. In some instances, the present disclosure is used for the collection, storage, research, application, or others, or combinations thereof biological agents or non-biological agents isolated or enriched from a sample.

As used herein, and unless otherwise specified, the term "about" means an acceptable error for a particular value as determined by one of ordinary skill in the art, which depends in part on how the value is measured or determined. In certain embodiments, the term "about" means within 1, 2, 3, or 4 standard deviations. In certain embodiments, the term "about" means within 30%, 25%, 20%, 15%, 10%, 9%, 8%, 7%, 6%, 5%, 4%, 3%, 2%, 1%, 0.5%, 0.1%, or 0.05% of a given value or range.

The apparatus, methods, and kits disclosed herein provide for one or more microbubbles adjacent to a biological agent to cause the biological agent to be buoyant in a liquid. In some instances, microbubbles can be surfactant microbubbles, lipid or phospholipid shell microbubbles, protein shell microbubbles (i.e. albumin shell), polymer microbubbles, polyelectrolyte microbubbles, or glass microbubbles, or combinations thereof.

In some instances microbubbles can be solid. In some instances, microbubbles can be hollow. In some instances, microbubbles can be porous. In some instances, microbubbles can comprise one or more layers or shells. In some instances, microbubbles can be composite, for example, comprising one or more individual particulates of a material or comprising one or more nanobubbles within a microbubble, or others. In some instances, the core of the microbubble comprising a gas can provide the buoyant property. In some instances, the material of the microbubble can provide the buoyant property. In some instances, microbubbles can be formed using methods known in the art.

In some instances, surfactant microbubbles can be formed from surfactants such as SPAN-40, TWEEN-40, or others. In some instances, lipid or phospho lipid microbubbles can be formed from natural lipids, phospholipids, sphingolipids, fatty acid modified lipids, head group modified lipids, fluorescent lipids, polymer lipids, cationic lipids, neutral lipids, or others. In some instances, microbubbles can be formed from DSPC/PEG40 stearate/DSPE-PEG3400-maleimide. In some instances, polymeric microbubbles can be formed from poly-lactic co-glycolic acid (PLGA), poly-caprolactone (PCL), polyvinylalcohol (PVA), combinations thereof or others. In some instances, microbubbles can also be formed from polysaccharides such as chitosan. In some instances, microbubbles can be utilized in a clinical setting. In some instances, the core of the microbubbles can comprise gas or liquid. In some instances, the core of the microbubbles can comprise perfluorohexane gas. In some instances, the core of the microbubble can comprise air.

In some instances, microbubbles can have surface hydrophobicity. In some instances, microbubbles can be durable under pressure. In some instances, microbubbles can disrupt at pressures much greater than ambient. In some instances, microbubbles can aggregate in a liquid. In some instances, microbubble aggregation improves isolation or enrichment from a sample of biological agents that are adjacent thereto microbubbles. In some instances, microbubbles can be buoyant in a liquid. In some instances, microbubble buoyancy improves isolation or enrichment from a sample of biological agents that are adjacent thereto microbubbles.

In some instances, microbubbles can have an outer diameter of about 2, 3, 4, 5, 6, 7, 8, 9, 10, 11, 12, 13, 14, 15, 16, 17, 18, 19, or about 20 microns. In some instances, microbubbles can have an outer diameter of about 1, 5, 10, 15, 20, 25, 30, 35, or about 40 microns. In some instances, microbubbles can have an outer diameter of about 0.15, 0.2, 0.25, 0.3, 0.35, 0.4, 0.45, 0.5, 0.55, 0.6, 0.65, or about 0.7 microns. In some instances, microbubbles can have an outer diameter of between about 1 micrometer and about 1 millimeter. In some instances, microbubbles can have an outer diameter of between about 0.2 microns and about 0.6 microns. In some instances, microbubbles can have an outer diameter of between about 1 micron and about 10 microns. In some instances, microbubbles can have an outer diameter of between about 2 microns and about 8 microns. In some instances, microbubbles can have an outer diameter of between about 2 microns and about 20 microns. In some instances, microbubbles can have an outer diameter of between about 2 microns and about 6 microns. In some instances, microbubbles can be monodisperse.

In some instances, microbubbles can be hollow. In some instances, microbubbles can be porous. In some instances, microbubbles can comprise a gaseous core. In some instances, microbubbles can comprise a liquid core with a density lower than the density of the liquid the microbubbles are dispersed in.

Selection markers can be adjacent to microbubbles such that specific biological agents in a sample will become adjacent thereto the microbubbles by interactions with one or more of the selection markers.

In some instances, selection markers can be antibodies, antibody fragments, antigens, hormone, growth factors, recombinant soluble receptors, transferrin, LDL, neurotransmitters, toxins, carbohydrates, lipids, nucleic acids, small molecules, aptamers, aptamer derivatives, dendrimers, proteins, peptides, polypeptides, nucleotides, polynucleotides or others or combinations thereof.

In some instances, a selection marker can be any molecule known to bind a cell surface marker. In some instances, a selection marker can be any known molecule to bind a stem cell surface marker. In some instances, a selection marker can be anti-CD34 or anti-CD133. In some instances, a selection marker can be any molecule known to bind AA4, AA4.1, P-gp, ABCB5, ABCG2, ALDH, alkaline phosphatase, alpha6-integrin, WNT2B, antithrombin III, asialo GM1, Bc1-2, beta1-integrin, c-kit (CD117), c-met, NCAM (CD56), CD105, CD133, CD166, CD29, CD30, CD31, siglec-3 (CD33), CD73, CD9, CD90, CK19, CLV3, ECMA-7, EDR1, EEC, FGF-4, Flk1, Flt3/Flk2, CD115, Glia2, Gli3, GSTA1, Her5, HSA, hsp25, Id2, IL-3Ralpha, KDR, keratin 15, keratin 19, kit, 1-selectin, lamin A/C, Lewis X antigen, LeX, Lgr5, Lrp4, MCM2, MCSP, nestin, neurofilament, NG2, NRP-1, nucleostemin, OC.3, Oct-4, OST-PTP, p21, p63, p75, PCLP, PCNA, PECAM, procalcitonin, RC1 antigen, Rex-1, Sca-1, SCF, Sox-9, SSEA-1, SSEA-3, SSEA-4, Stat3, StatS, Stra8, Stro-1, Thy-1, Tra-1-60, VEGFR-2, or Zac1 or combinations thereof, or others.

In some instances, a selection marker can be any known molecule to bind tumor or cancer cell surface marker. In some instances, a selection marker can be anti-EpCAM. In some instances, a selection marker can be anti-Her2. In some instances, a selection marker can be anti-EGFR. In some instances, a selection marker can be anti-CEA. In some instances, a selection marker can be any molecule known to bind alpha-fetoprotein (AFP), beta-2-microglobulin (B2M), beta-human chorionic gonadotropin (Beta-hCG), carcinoembryonic antigen (CEA), CD20, chromogranin A (CgA), Her-2, Kit, or prostate-specific antigen (PSA) or combinations thereof or others.

In some instances, a selection marker can be any known molecule to bind an immune cell surface marker. In some instances, a selection marker can be anti-CD3, anti-CD4, anti-CD8, or others. In some instances, a selection marker can be any molecule known to bind CD3, CD4, CD8, CD25, CD45, CD2, CD5, CD6, CD27, CD31, CD25, CD69, CD28, CD152, CD154, CD19, CD20, CD40, CD134, CD83, CMRF-44, CMRF-56, OX40L, DEC-205, CD11c, F4/80, CD11b, MHCII, BDCA-1, CD68, or DC-SIGN, or combinations thereof, or others. In some instances, a selection marker known to bind an immune cell surface marker can be used to isolate or enrich cells for immunotherapy. In these instances, cells for immunotherapy can be used to induce, enhance, or suppress an immune response. In these instances, cells for immunotherapy in cancer can be used to induce an immune response towards cancer cells, such that the immune system can reject or destroy tumor or cancer cells. In these instances, cells for immunotherapy in cancer can reject or destroy tumor or cancer cells. In these instances, cells for immunotherapy in cancer can stimulate an immune response to reject or destroy tumor or cancer cells.

One or more selection markers can be adjacent thereto to the surface of one or more microbubbles. In some instances, one or more selection markers can be attached to the surface of one or more microbubbles. In some instances, one or more selection markers can be inserted into the outer shell of the microbubble. In some instances, one or more selection markers can be inserted into the core of the microbubble. In some instances, one or more selection markers can be inserted into both the outer shell and core of the microbubble. In some instances, one or more selection markers can be attached to the outer surface of the microbubble by nucleophilic conjugate addition. In some instances, one or more selection markers can be attached to the outer surface of the microbubble by Michael addition. In some instances, one or more selection markers can be attached to the outer surface of the microbubble by a linking group that can be directly attached to the one or more microbubbles. In some instances, the linking group can be an antibody fragment, such as Fc fragment specific IgG. In some instances, more than one linking group can attach the one or more selection markers to the outer surface of the microbubble.

In some instances, selection markers can be adjacent to the surface of one or more microbubbles. In some instances, selection markers can be uniformly distributed adjacent to the outer surface of one or more microbubbles. In some instances, selection markers can be adjacent to one or more discrete regions of the outer surface of microbubbles. In some instances, selection markers can be patterned adjacent to the surface of microbubbles.

In some instances, about 1, 100, 500, 1,000, 5,000, 10,000, 50,000, 100,000, 125,000, 150,000, 175,000, 200,000, 225,000, 250,000, 275,000, 300,000, 325,000, 350,000, 375,000, 400,000, 425,000, 450,000, 475,000, 500,000, 525,000, 550,000, 575,000, 600,000 or more selection markers can be adjacent to the outer surface of a single microbubble. In some instances, between about 200,000 and about 500,000 selection markers can be adjacent to the outer surface of a single molecule. In some instances, between about 300,000 and about 400,000 selection markers can be adjacent to the outer surface of a single microbubble. In some instances, at least about 5,000 selection markers can be adjacent to the outer surface of a single microbubble. In some instances, at least about 10,000 selection markers can be adjacent to the outer surface of a single microbubble. In some instances, at least about 100,000 selection markers can be adjacent to the outer surface of a single microbubble.

Isolation, enrichment, or depletion of distinct biological agents can include microbubbles with a first set and a second set of selection markers on each microbubble. In some instances, the first set and the second set of selection markers are different. For example, a first set of selection markers for CD133 and a second set of selection markers for CD34 can both be adjacent to the same microbubble.

Simultaneous isolation or enrichment of two distinct biological agents can include microbubbles with a first set and a second set of selection markers. In some instances, the first set and the second set of selection markers are different. For example, a first set of selection markers for CD45 can be adjacent to a first microbubble and a second set of selection markers for CD34 can be adjacent to a second microbubble. In some instances, more than one type of selection marker can be adjacent to the surface of each of the one or more microbubbles.

Biological agents or non-biological agents can be isolated or enriched from a sample. In some instances, biological agents or non-biological agents can be depleted from a sample. In some instances, the sample can be a clinical sample. In some instances, the sample can be a laboratory sample. In some instances, a sample can be an industrial sample. In some instances, the sample can be obtained from a subject. In some instances, the sample can be obtained from the user. In some instances, the sample can be previously manipulated such as diluted, frozen, sterilized, or others.

A sample can be tissue, blood, bone marrow, urine, saliva, cerebrospinal fluid, seminal fluid, sputum, stool, joint fluid, lymph, amniotic fluid, bile, ascites, pleural effusion, or others. In some instances, a sample can be a tumor or cancer tissue. In some instances, a sample can be fluid within and around a tumor or cancer tissue. In some instances, a sample can be a blood sample. In some instances, a blood sample can be umbilical cord blood.

Non-biological agents isolated or enriched from a sample can include but are not limited to chemical agents, industrial agents, agricultural agents, manufacturing agents or others, or combinations thereof. In some instances, non-biological agents can be polymers, organic compounds, inorganic compounds, or others. In some instances, non-biological agents can be a solid, liquid, or gas. In some instances, the non-biological agent isolated can be an impurity. In some instances, the non-biological agent can be an elemental metal or a metal alloy. In some instances, the non-biological agent can be a pharmaceutical composition.

In some instances, the non-biological agent can be a narcotic particle in a blood sample or urine sample obtained from a subject. In instances wherein the non-biological agent can be a narcotic particle, the sample from the subject can be analyzed by a law enforcement person, a crime lab person, or other criminal justice personnel. In some instances, the narcotic particle can be cocaine or amphetamine, or others. In some instances, specific antibodies or other ligands to narcotics can be adjacent thereto microbubbles to capture the narcotic particles from the blood or urine sample. In some instances, ELISA assays can determine the amount of narcotic particles adjacent thereto the microbubbles.

Biological agents isolated or enriched from a sample can include but are not limited to cells, cell fragments, organelles, bacteria, viruses, fungi, parasites, proteins, peptides, polypeptides, nucleotides, polynucleotides, DNA, RNA, or amino acids. In some instances, biological agents can be cells. In some instances, biological agents can be cell lines. In some instances, biological agents can be primary cells. In some instances, biological agents can be rare cells in a sample, such as less than 0.001%, 0.01%, or 0.1% the total cell population in the sample. In some instances, the biological agents can be immune cells for immunotherapy. In some instances, biological agents can be hematopoietic stem cells. In some instances, biological agents can be circulating tumor cells. In some instances, cells can be 4T1 mouse cells, BxPC3 pancreatic adenocarcinoma cells, ASPC1 pancreatic adenocarcinoma cells, A549 lung cancer cells, PC3 prostate cancer cells, KG1a cells, or others.

Figure 1B:
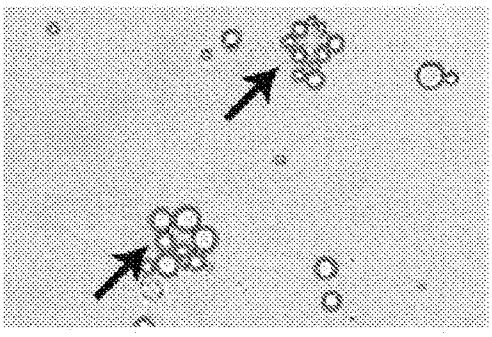

Selection markers can be adjacent to microbubbles such that specific biological agents in a sample will become adjacent thereto the microbubbles by interactions with one or more of the selection markers. FIG. 1A-B show the synthesis and characterization of microbubbles with selection marker adjacent thereto with microscopic images to show microbubbles adjacent thereto cells after incubation with microbubbles.

Microbubbles can be adjacent thereto biological agents of a sample. Microbubbles can attach to a biological agent by a selection marker adjacent thereto the outer surface of the microbubble. Microbubbles can attach to a biological agent by binding a selection marker to a surface marker on the surface of the biological agent. Microbubbles can attach to a biological agent by binding a selection marker to a binding region on the surface of the biological agent. In some instances, a selection marker binds a cell surface marker, thereby attaching the microbubble to a cell. In some instances, a selection marker binds a binding region of a protein, polypeptide or peptide, thereby attaching the microbubble to the protein, polypeptide, or peptide.

In some instances, the biological agents to be enriched or isolated from a sample can comprise other components. For example, a sample comprising biological agents such as stem cells to be enriched or isolated may also comprise blood cells, antibodies, and others. In some instances, the biological agents to be enriched or isolated can comprise 0.001%, 0.01%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12% 13%, 14%, 15%, 16%, 17%, 18%, 19%, 20%, 21%, 22%, 23%, 24%, 25% or less the total number of components in a sample. In some instances, the biological agents to be enriched or isolated can comprise less than 20% of the sample. In some instances, the biological agents to be enriched or isolated can comprise less than 10% of the sample. In some instances, the biological agents to be enriched or isolated can comprise less than 5% of the sample. In some instances, the biological agents to be enriched or isolated can comprise less than 1% of the sample. In some instances, the biological agents to be enriched or isolated can be about 100 biological agents or less per 10 mL of sample. In some instances, the biological agents to be enriched or isolated can be about 100 biological agents or less per 9 mL of sample. In some instances, the biological agents to be enriched or isolated can be about 100 biological agents or less per 8 mL of sample. In some instances, the biological agents to be enriched or isolated can be about 100 biological agents or less per 7 mL of sample. In some instances, the biological agents to be enriched or isolated can be about 100 biological agents or less per 6 mL of sample. In some instances, the biological agents to be enriched or isolated can be about 100 biological agents or less per 5 mL of sample.

In some instances, the percent of biological agents with one or more microbubbles adjacent thereto following incubation can be about 60%, 65%, 70%, 75%, 80%, 85%, 90%, 95%, 96%, 97%, 98%, 99% or more. In some instances, the percent of biological agents with one or more microbubbles adjacent thereto can be 100%. In some instances, the percent of biological agents with one or more microbubbles adjacent thereto can be about 85% to about 95%. In some instances, the percent of biological agents with one or more microbubbles adjacent thereto can be about 80% to about 95%. In some instances, the percent of biological agents with one or more microbubbles adjacent thereto can be at least about 85%. In some instances, the percent of biological agents with one or more microbubbles adjacent thereto can be at least about 90%.

In some instances, one or more biological agents can be incubated with one or more microbubbles such that following a period of incubation the one or more microbubbles can be adjacent thereto one or more biological agents. In some instances, the period of incubation can be about 1, 2, 3, 4, 5, 6, 7, 8, 9, 10, 11, 12, 13, 14, or about 15 minutes or more. In some instances, the period of incubation can be about 1 minute or less. In some instances, the period of incubation can be about 5 minutes or less. In some instances, the period of incubation can be about 10 minutes or less. In some instances, the period of incubation can be about 15 minute or less. In some instances, the period of incubation can be between about 1 minute and about 5 minutes. In some instances, the period of incubation can be between about 1 minute and about 10 minutes.

In some instances, one or more microbubbles adjacent to a biological agent can cause the biological agent to be sufficiently buoyant in a liquid. In some instances, sufficiently buoyant can be biological agents adjacent to microbubbles that are floating on the top of a liquid at a liquid atmosphere interface. In some instances, sufficiently buoyant can be biological agents adjacent to microbubbles that are floating within a liquid at a depth above complete sedimentation to the bottom of the liquid. In some instances, sufficiently buoyant can be biological agents adjacent to microbubbles that are floating within a liquid away from a liquid-liquid interface with a second liquid of different density. In some instances, microbubbles alone can be buoyant. In some instances, biological agents adjacent to one or more microbubbles can be buoyant. In some instances, the buoyancy of a biological agent depends of the number of microbubbles adjacent thereto. In some instances, microbubbles can be buoyant in a first liquid but not in a second liquid.

In some instances, one or more microbubbles adjacent to a biological agent can cause the biological agent to be buoyant in a liquid. In some instances, the number of microbubbles needed to be adjacent to a biological agent to cause the biological agent to be buoyant in a liquid varies by the radius of the microbubble. The smaller the radius of the microbubble, the more microbubbles needed to cause a biological agent to be buoyant. In some instances, the number of microbubbles needed to be adjacent to a biological agent to cause the biological agent to be buoyant in a liquid varies by the size, shape, composition, surface area, weight, or charge of the biological agent.

In some instances, about 1, 2, 3, 4, 5, 6, 7, 8, 9, 10, 11, 12, 13, 14, 15, 16, 17, 18, 19, or about 20 microbubbles or more can cause a biological agent to be buoyant. In some instances, more than about 20 microbubbles can cause a biological agent to be buoyant. In some instances, at least 2 microbubbles can cause a biological agent to be buoyant. In some instances, between about 2 and about 8 microbubbles can cause a biological agent to be buoyant. In some instances, between about 10 and about 20 microbubbles can cause a biological agent to be buoyant. In some instances, about 2 microbubbles with an outer diameter of about 3 microns can cause a biological agent to be buoyant. In some instances, about 20 microbubbles with an outer diameter of about 1.5 microns can cause a biological agent to be buoyant.

In some instances, the liquid can an aqueous solution. In some instances, the aqueous solution can be phosphate buffered saline. In some instances, the liquid can be blood. In some instances, the liquid can be sterile. In some instances, a sample can be diluted with a liquid. In some instances, a liquid can be added to a sample. In some instances, a sample can be diluted with a liquid to enhance the viability of the biological agents within the sample. In some instances, addition of liquid to a sample causes microbubbles to float.

In some instances, the liquid can be the sample itself. In some instances, the liquid can be blood, urine, saliva, cerebrospinal fluid, seminal fluid, sputum, stool, joint fluid, lymph, amniotic fluid, bile, ascites, pleural effusion, or other bodily fluids. In some instances, the liquid has a density of between about 0.9 and about 1.1 grams per cubic centimeter. In some instances, the liquid has a density of between about 0.95 and about 1.05 grams per cubic centimeter. In some instances, the liquid has a density of about 1 gram per cubic centimeter.

Following a period of incubation, one or more microbubbles can be adjacent thereto the one or more biological agents of a sample. In some instances, the ratio of a single biological agent adjacent thereto microbubbles can be about 1:1000. In some instances, the ratio can be about 1:100. In some instances, the ratio can be about 1:500. In some instances, the ratio can be about 1:2000. In some instances, the ratio can be about 1:1, 1:10, 1:25, 1:50, 1:55, 1:60, 1:65, 1:70, 1:75, 1:80, 1:85, 1:90, 1:95, 1:100, 1:105, 1:110, 1:115, 1:120, 1:125, 1:130, 1:135, 1:140, 1:145, 1:150, 1:155, 1:160, 1:165, 1:170, 1:175, 1:180, 1:185, 1:190, 1:195, 1:200, 1:250, 1:300, 1:350, 1:400, 1:450, 1:500, 1:550, 1:600, 1:650, 1:700, 1:750, 1:800, 1:850, 1:900, 1:950, 1:1000, 1:1100, 1:1200, 1:1300, 1:1400, 1:1500, or about 1:2000. In some instances, the ratio can be between about 1:900 and about 1:1100. In some instances, the ratio can be between about 1:500 and about 1:2000. In some instances, the ratio can be between about 1:500 and about 1:1500.

One or more biological agents can be isolated using the apparatus, methods, and kits disclosed herein. In some instances, a single set of biological agents can be isolated. In some instances, the single set can be homogeneous, such as a cell population wherein each cell expresses the sample level of a cell surface marker. In some instances, the single set can be heterogeneous, such as a cell population wherein each cell expresses the same cell surface marker, but at different levels. In a first example, a single set of biological agents such as circulating tumor cells expressing surface marker EpCAM can be isolated from a sample that comprises the circulating tumor cells and other cell types in a blood sample using the apparatus, methods, and kits disclosed herein. In a second example, a single set of biological agents such as bovine serum albumin can be isolated from a sample that comprises the bovine serum albumin and other proteins using the apparatus, methods, and kits disclosed herein.

In some instances, a first set and a second set of biological agents can be isolated from a sample using the apparatus, methods, and kits disclosed herein. In some instances, the first and second set of biological agents can be different. In some instances, 2, 3, 4, 5 or more sets of biological agents can be isolated using the apparatus, methods, and kits disclosed herein. In some instances, 3 sets of biological agents can be isolated using the apparatus, methods, and kits disclosed herein. For example, a first set of tumor cells expressing cell surface marker EpCAM and a second set of tumor cells expressing cell surface marker CEA (carcinoembryonic antigen) or a third set of biological agents expressing both EpCAM and CEA can be isolated from a sample using the apparatus, methods, and kits disclosed herein.

Microbubbles that are adjacent to biological agents can be dissociated from the biological agents by microbubble disruption. In some instances, microbubbles are disrupted after enrichment or isolation of biological agents. In some instances, microbubbles are disrupted at any point after becoming adjacent to biological agents. In some instances, all microbubbles are disrupted. In some instances, a portion of microbubbles are disrupted. In some instances, at least 60%, 65%, 70%, 75%, 80%, 85%, 90%, 95% or more of the microbubbles adjacent to the biological agents are disrupted. In some instances, more than 95% of microbubbles adjacent to the biological agents are disrupted. In some instances, between about 90% to about 95% of the microbubbles adjacent to the biological agents are disrupted.

In some instances, microbubbles can be disrupted chemically or thermally. In some instances, microbubbles can be disrupted by sonication, vacuum application, application of organic solvents, application of surfactants, or increasing ambient pressure, or others. In some instances, microbubbles are disrupted by degradation, such as hydrolytic degradation or bio-erosion. In some instances, microbubbles can be disrupted by pH changes or temperature changes.

In some instances, microbubbles can be disrupted by sonication. In some instances, microbubbles can be disrupted by sonication for at least about 1, 2, 3, 4, 5, 6, 7, 8, 9, or about 10 seconds or more. In some instances, microbubbles can be disrupted by sonication for at least about 2 seconds. In some instances, microbubbles can be disrupted by sonication for at least about 5 seconds. In some instances, microbubbles can be disrupted by sonication for at least about 10 seconds. In some instances, microbubbles can be disrupted by sonication using a water bath sonicator.

In some instances, microbubbles can be disrupted by increasing ambient pressure. In some instances, increasing ambient pressure can be done by air compression. In some instances, the apparatus, methods, and kits disclosed herein can provide air compression of 3 atm for 5 minutes. In some instances, the apparatus, methods, and kits disclosed herein can provide air compression of 3 atm for 8 minutes. In some instances, the apparatus, methods, and kits disclosed herein can provide air compression of 3 atm for 10 minutes. In some instances, the apparatus, methods, and kits disclosed herein can provide air compression of 2 atm for 5 minutes. In some instances, the apparatus, methods, and kits disclosed herein can provide air compression of 2 atm for 8 minutes. In some instances, the apparatus, methods, and kits disclosed herein can provide air compression of 2 atm for 10 minutes. In some instances, the apparatus, methods, and kits disclosed herein can provide air compression of 4 atm for 5 minutes. In some instances, the apparatus, methods, and kits disclosed herein can provide air compression of 4 atm for 8 minutes. In some instances, the apparatus, methods, and kits disclosed herein can provide air compression of 4 atm for 10 minutes. In some instances, the apparatus, methods, and kits disclosed herein can provide air compression of about 1.5, 2, 2.5, 3, 3.5, 4, 4.5, 5 atm or more. In some instances, the apparatus can provide air compression of between about 2 atm and about 4 atm. In some instances, the apparatus can provide air compression of between about 2 atm and about 4 atm for about 3 minutes to about 10 minutes. In some instances, the apparatus can provide air compression for about 1, 2, 3, 4, 5, 6, 7, 8, 9, 10, 11, 12, 13, 14, 15 minutes or more.

In some instances, the air compression provided for disruption of microbubbles does not affect cell viability. In some instances, more than about 99% of cells remain viable following air compression. In some instances, more than about 98% of cells remain viable following air compression. In some instances, more than about 97% of cells remain viable following air compression. In some instances, cells remain viable for at least 2 hours following air compression. In some instances, cells remain viable for at least 8 hours following air compression. In some instances, cells remain viable for at least 18 hours following air compression. In some instances, cells remain viable for at least 24 hours following air compression.

Of the total biological agents in a sample, the apparatus, methods, and kits disclosed herein can provide a recovery efficiency of at least about 90%. In some instances, the recovery efficiency can be at least about 95%. In some instances, the recovery efficiency can be at least about 98%. In some instances when biological agents can be cells, the recovery efficiency can be at least about 90% with cell viability at least about 95%. In some instances, the recovery efficiency can be at least about 80% with cell viability at least about 90%. In some instances, the recovery efficiency can be at least about 95% with cell viability at least about 90%. In some instances, the recovery efficiency can be at least about 95% with cell viability at least about 85%.

Figure 2:
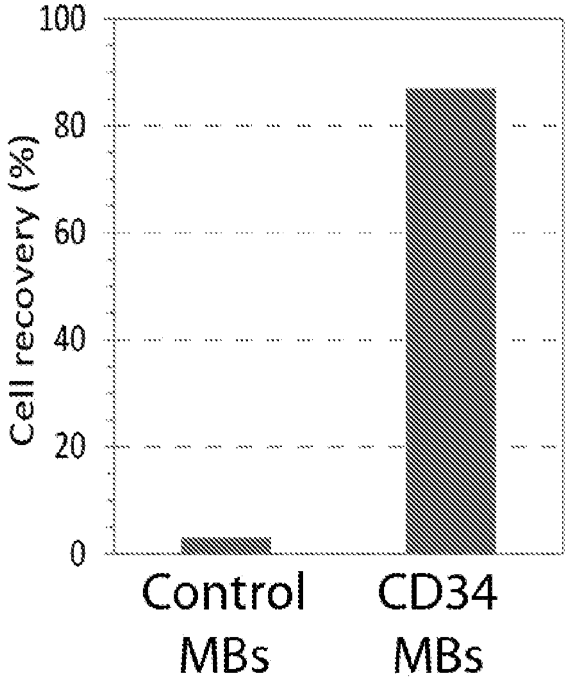
FIG. 2 illustrates the percent recovery of CD34+KG1a cells incubated with either a) microbubbles lacking any selection marker (control MBs) or with b) CD34-microbubbles (CD34 MBs).

FIG. 2 shows the percent recovery of CD34+ KG1a cells incubated with either microbubbles lacking any selection marker, or incubated with CD34-microbubbles demonstrating 87% recovery of CD34+ KG1a cells using the CD34-microbubbles.

Figures 3A, 3B:
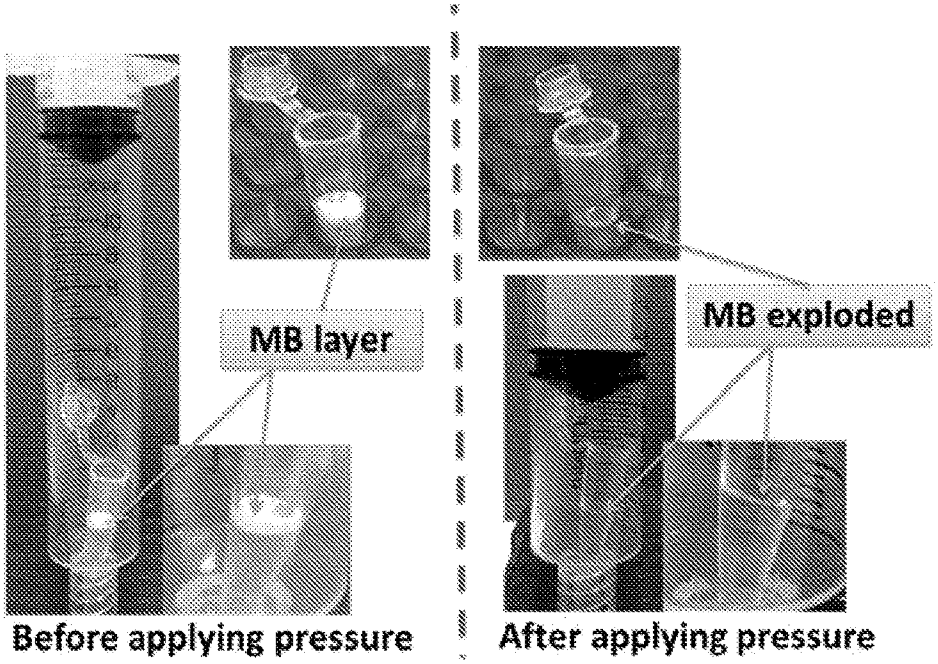
FIG. 3A illustrates the microbubble layer before applying pressure and the microbubble layer disrupted after applying pressure and 3B illustrates cell viability following microbubble disruption using high ambient pressure.

FIG. 3 shows cell viability following microbubble disruption using high ambient pressure. FIG. 3A shows a sample container with a microbubble layer before and after applying pressure. FIG. 3B shows the time of high pressure application and the resulting cell viability in both the control and pressure-treated group.

In some instances, following microbubble disruption, isolated or enriched cells reattach to a tissue culture dish and proliferate following isolation from blood using the methods disclosed herein.

The apparatus, methods, and kits disclosed herein provide for enrichment or isolation of biological agents from a sample using a sample container. The sample container can comprise an inner volume to hold the sample and microbubbles. The inner volume can be smooth and curved. The sample container can comprise a length longer than a width. The sample container can comprise a cylinder with two ends. The cylindrical sample container can comprise an open end and opposite the open end can be a tapered end. In some instances, the tapered end can be a cone-shaped end. In some instances, the sample container can be a test tube or a centrifuge tube with an open end and a tapered end with a conical, flat, or rounded tip. In some instances, the sample container can be a 50 mL tube. In some instances, the sample container can be a 15 mL tube. In some instances, the sample container can be a 10 mL tube. In some instances, the sample container can be a 1 mL tube.

In some instances, the sample container can be glass, such as borosilicate glass, fused silica, quartz glass, KIMAX®, PYREX®, or ZERDOUR®, or others. In some instances, the sample container can be plastic, such as polyethylene, polystyrene, polypropylene, polytetrafluoroethylene (PTFE), polyurethane (PU), polyvinylchloride (PVC), EPDM, fluoroelastomer, neoprene, nitrile, or nylon or others. In some instances, the sample container can be fabricated by 3D printing. In some instances, the sample container can be fabricated by injection molding. In some instances, the sample container can be reusable. In some instances, the sample container can be disposable. In some instances, the sample container can be a one-time use container. In some instances, the sample container can be sterile. In some instances, the inner volume of the sample container can be sterilized.

The angle of the container spout can be determined by measuring the angle relative to the horizontal axis of the sample container. In some instances, the angle of the container spout relative to horizontal axis of the sample container can be less than 90 degrees. In some instances, the angle can be about 85, 80, 75, 70, 65, 60, 55, 50, 45, 40, 35, 30, 25, 20, 15, 10, or 5 degrees. In some instances, the angle can be between about 15 degrees to about 50 degrees. In some instances, the angle can be between about 15 degrees to about 35 degrees. In some instances, the angle can be between about 20 degrees to about 50 degrees. In some instances, the angle can be more acute than the angle of the angled tip of the tapered end.

In some instances, the open end of the sample container opposite the tapered end can be flat wherein the entire circumference of the open end can be equidistant to a flat tapered end. In some instances, the tip of the tapered end of the sample container can form a perpendicular angle relative to the horizontal axis of the sample container. In some instances, a plunger can be inserted into the open end of the sample container.

Figure 10:
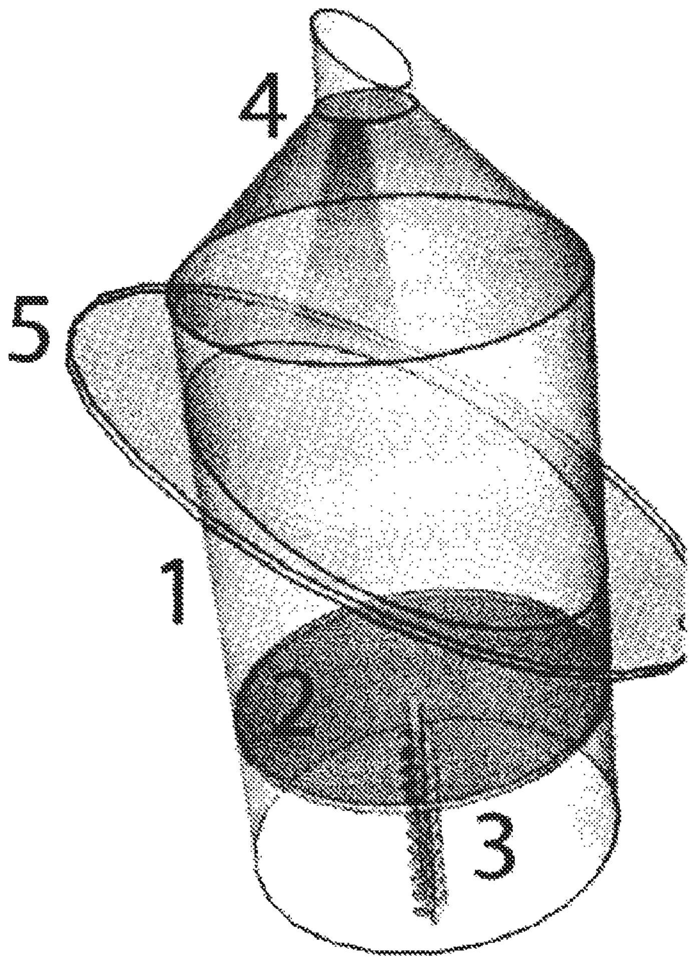
FIG. 10 illustrates an angled tip of the tapered end of a sample container.

In some instances, the tapered end can be open. In some instances, the tapered end can be adjacent to a needle. In some instances, the tapered end can be adjacent to a container spout. In some instances, the tapered end can be flat wherein the entire circumference of the tapered end can be equidistant to the flat open end. In some instances, the tip of the tapered end of the sample container can form a perpendicular angle relative to the horizontal axis of the sample container. In some instances, the tapered end can comprise an angled tip, FIG. 10.

The angle of the angled tip on the tapered end can be determined by measuring the angle relative to the horizontal axis of the sample container. In some instances, the angle of the angled tip on the tapered end can be less than about 90 degrees. In some instances, the angle can be less than about 80 degrees. In some instances, the angle can be less than about 70 degrees. In some instances, the angle can be less than about 60 degrees. In some instances, the angle can be less than about 50 degrees. In some instances, the angle can be less than about 40 degrees. In some instances, the angle can be less than about 30 degrees. In some instances, the angle can be less than about 20 degrees. In some instances, the angle can be less than about 10 degrees. In some instances, the angle can be less than about 5 degrees. In some instances, the angle can be between about 1 degree and about 5 degrees. In some instances, the angle can be between about 1 degree and about 10 degrees. In some instances, the angle can be between about 5 degrees and about 10 degrees. In some instances, the angle can be between about 1 degree and about 20 degrees. In some instances, the angle can be between about 1 degree and about 30 degrees. In some instances, the angle can be between about 1 degree and about 40 degrees. In some instances, the angle can be between about 1 degree and about 50 degrees. In some instances, the angle can be between about 5 degrees to about 40 degrees. In some instances, the angle can be between about 5 degrees to about 10 degrees. In some instances, the angle can be about 35 degrees. In some instances, the angle can be about 30 degrees. In some instances, the angle can be about 40 degrees. In some instances, the angle can be about 1, 5, 10, 15, 20, 25, 30, 35, 40, 45, 50, 55, 60, 65, 70, 75, 80, or about 85 degrees.

In some instances, the angle of the sample container shaft can be 90 degrees. In some instances, the angle of the sample container shaft can be between about 85 and about 95 degrees.

In some instances, the sample can be added directly to the inner volume of the sample container for enrichment or isolation of the biological agents. In some instances, the sample can be diluted before or after being added to the sample container. In some instances, the sample can be added directly to the inner volume of the sample container without centrifugal concentration. In some instances, the total volume of a sample can be added to the sample container. In some instances, the sample can be divided into separate subvolumes that can be separated added to separate sample containers. In some instances, the sample can be further diluted with a liquid prior to being added to the sample container.

In some instances, the sample volume that can be accommodated by the sample container can be about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 105, 110, 115, 120, 125, 130, 135, 140, 145, 150, 155, 160, 165, 170, 175, 200, 250, 300, 350, 400, 450, 500 mL or more. In some instances, the total sample volume can be less than about 1 mL. In some instances, the total sample volume can be less than about 5 mL. In some instances, the total sample volume can be less than about 10 mL. In some instances, the total sample volume can be less than about 15 mL. In some instances, the total sample volume can be less than about 50 mL. In some instances, the total sample volume can be less than about 100 mL. In some instances, the total sample volume can be less than about 200 mL. In some instances, the total sample volume can be less than about 500 mL.

In some instances, the total sample volume can be between about 1 mL and about 5 mL. In some instances, the total sample volume can be between about 1 mL and about 10 mL. In some instances, the total sample volume can be between about 1 mL and about 15 mL. In some instances, the total sample volume can be between about 1 mL and about 50 mL. In some instances, the total sample volume can be between about 1 mL and about 100 mL.

In some instances, the inner surface of the sample container can be hydrophobic to promote droplet formation at the tip of the tapered end during collection of the biological agents from the sample container. In some instances, a hydrophobic layer can be adjacent to the inner surface of the sample container. In some instances, a hydrophobic layer can be coated onto the inner surface of the sample container.

In some instances, the inner surface of the sample container comprises a material making the inner surface hydrophobic. In some instances, an amphiphilic agent can be coated on the inner surface of the sample container to provide a hydrophobic layer. In some instances, the hydrophobic layer can comprise a siliconizing fluid such as SURFASIL™ OR AQUASIL™. In some instances, the hydrophobic layer can comprise paraffin, such as paraffin wax, kerosene, liquid paraffin, mineral oil, or petroleum jelly, or combinations thereof. In some instances, the hydrophobic layer can comprise one or more of polytetrafluoroethylene (PTFE) (such as TEFLON®), perfluoroalkoxy (PFA), or fluorinated ethylene propylene (FEP), or others. In some instances, the hydrophobic layer can comprise one or more poloaxmers such as SYNPERONICS®, KOLLIPHOR®, or PLURONIC® (such as F68 or F127 or others).

In some instances, the entire inner surface of the surface container can be hydrophobic. In some instances, a portion of the inner surface can be hydrophobic. In some instances, about 1%, 2%, 3%, 4%, 5%, 6%, 7%, 8%, 9%, 10%, 15%, or about 20% of the inner surface can be hydrophobic. In some instances, the portion of the inner surface that can be hydrophobic can be the tapered neck. In some instances, the portion of the inner surface that can be hydrophobic can be the container top opening. In some instances, the portion of the inner surface that can be hydrophobic can be the tapered neck and container top opening.

In some instances, the inner surface of the sample container can be hydrophilic to prevent microbubbles from attaching, sticking, or aggregating at the inner surface. In some instances, a sample container comprises a material such as glass to provide an inner surface that can be hydrophilic. In some instances, the inner surface of the sample container can have a hydrophilic layer adjacent thereto. The adjacent hydrophilic layer can attach to the sample container by covalent bond, ionic bond, electrostatic interactions, van de Waal forces, or others. In some instances, an amphiphilic agent can be coated on the inner surface of the sample container to provide a hydrophilic layer. In some instances, bovine serum albumin, polyurethane resin, polyvinylpyrrolidone (PVP), hyaluronic acid polyacrylate, or polyurethane polyacrylate, or combinations thereof, or others can provide a hydrophilic layer adjacent to the inner surface of the sample container.

In some instances, the entire inner surface of the sample container can be hydrophilic. In some instances, a portion of the inner surface can be hydrophilic. In some instances, about 75%, 80%, 85%, 90%, 95%, 96%, 97%, 98%, 99% or more of the inner surface can be hydrophilic. In some instances, the portion of the inner surface that can be the tapered neck can be not hydrophilic. In some instances, the portion of the inner surface that can be the container top opening can be not hydrophilic. In some instances, the portion of the inner surface that can be the tapered neck and the container top opening can be not hydrophilic.

The apparatus, methods, and kits disclosed herein can localize one or more biological agents adjacent to one or more microbubbles such that the biological agents can be isolated or enriched. In some instances, the sample container can separate the biological agents adjacent to the microbubbles by separation into a removable harvesting cap assembly.

Figure 4:
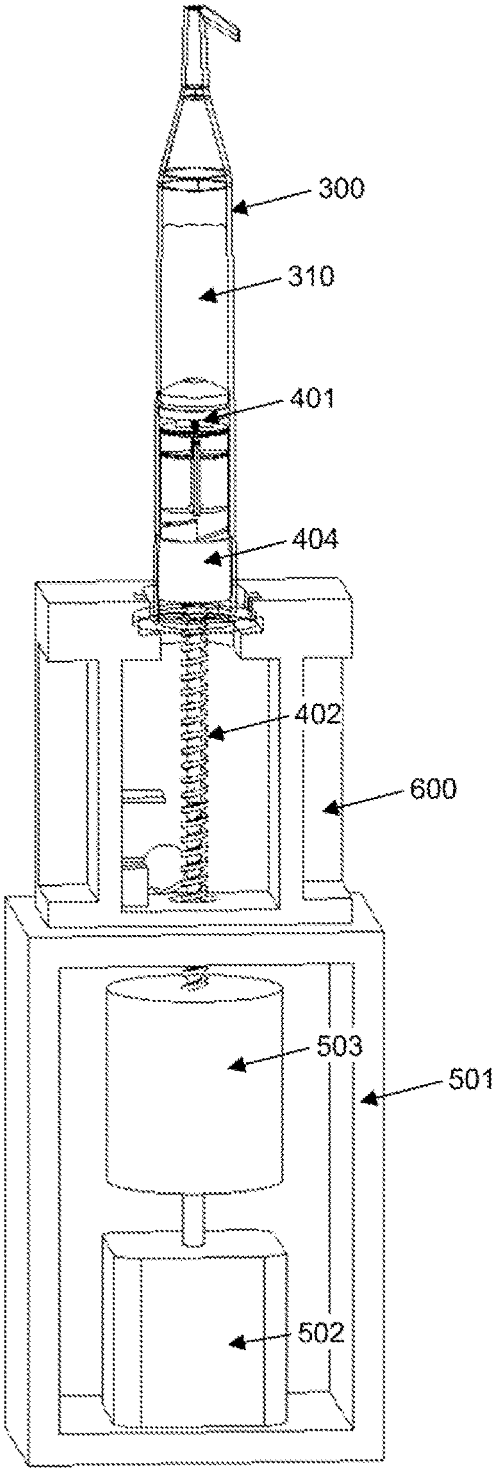
FIG. 4 illustrates one embodiment of the apparatus of the present disclosure.

FIG. 4 shows one embodiment of the apparatus. A sample container 300 can contain an inner volume, 301, comprising a sample, one or more microbubbles with one or more selection markers adjacent thereto, a liquid, or combinations thereof, 310. A plunger, 401, can be inserted into the sample container 300 at the open end, 304, opposite the tapered end, 303. The plunger, 401, can be driven by a drive screw, 402, that can be housed in a container mount, 600, by contacting the drive screw 402 to the plunger engagement adapter, 404. The bottom flange, 308, of the sample container can also be housed in the container mount, 600. A mechanical convertor, 503, converting motor shaft rotation into linear translation of the plunger, can be housed in the apparatus closure, 501. A drive motor, 502, housed in the apparatus enclosure, can automatically drive the plunger via the mechanical convertor, 503.

In some instances, the drive screw can be metal. In some instances, the drive screw can be non-metal. In some instances, the drive screw can be plastic. In some instances, the drive screw can be fabricated by 3D printing.

Figure 5:
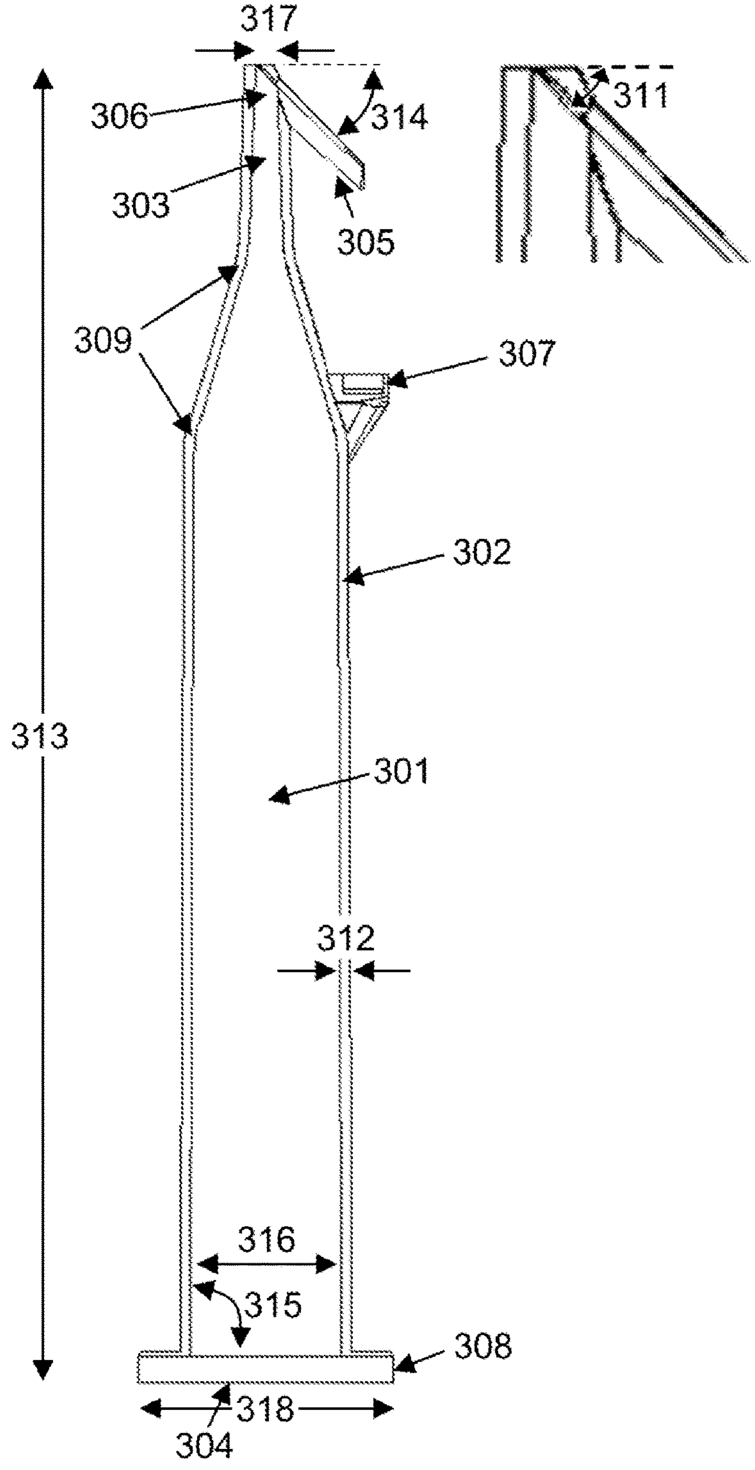
FIG. 5 illustrates one embodiment of the sample container of the apparatus.

FIG. 5 shows the sample container, 300. The sample container can be formed of any container material, 302, as disclosed herein. The sample container can have a tapered end, 303, and an open end 304 into which a plunger can be inserted. The sample container can comprise a container spout, 305 at the tip of the opening, 306, of the tapered end. The container spout, 305 can form an acute angle relative to the horizontal axis of the sample container, 314. The tip of the tapered end can form an acute angle, 311, relative to the horizontal axis of the sample container. The acute angle, 311, of the tip can be the same as the acute angle of the container spout, 314. The acute angle, 311, of the tip can be different than the acute angle of the container spout, 314. The acute angle, 311, of the tip can be more acute than the acute angle of the container spout, 314. The sample container can have a collection container, 307, to collect 310 from the container spout, 305. The collection container can be mounted onto the sample container. The collection container can be mounted on the outer surface of the sample container close to the bottom end of the container spout.

The sample container can comprise a bottom inner diameter, 316, as disclosed herein. The sample container can comprise a top inner diameter, 317, as disclosed herein. The sample container can comprise a bottom outer diameter including the bottom flange, 308, as disclosed herein. The sample container can comprise a wall thickness, 312, as disclosed herein. The sample container can comprise a container height, 313, as disclosed herein. The sample container can comprise a spout angle, 314, as disclosed herein. The sample container can comprise a main container shaft angle, 315, as disclosed herein. The transition from the inner diameter, 316 at the open end 304 to the tapered end, 303, can be a curved inner surface, 309, for smooth angle transition between the two ends.

In some instances, the bottom inner diameter, 316, of the sample container can be between about 10 mm and about 20 mm. In some instances, the bottom inner diameter of the sample container can be about 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or about 25 mm or more. In some instances, the bottom inner diameter of the sample container can be about 10 mm. In some instances, the bottom inner diameter of the sample container can be about 15 mm. In some instances, the bottom inner diameter of the sample container can be about 18 mm. In some instances, the bottom inner diameter of the sample container can be about 20 mm.

In some instances, the top inner diameter, 317, of the sample container can be less than the bottom inner diameter. In some instances, the top inner diameter can be about 3 mm. In some instances, the top inner diameter can be about 4 mm. In some instances, the top inner diameter can be about 2 mm. In some instances, the top inner diameter can be between about 2 mm and about 5 mm. In some instances, the top inner diameter can be between about 1 mm and about 5 mm. In some instances, the top inner diameter can be between about 1 mm and about 3 mm. In some instances, the top inner diameter can be about 1, 1.25, 1.5, 1.75, 2, 2.25, 2.5, 2.75, 3, 3.25, 3.5, 3.75, 4, 4.25, 4.5, 4.75, 5, 5.25, or 5.5 mm. In some instances, the top inner diameter can be at least 1 mm.

In some instances, the bottom outer diameter, 318, of the sample container can be more than the bottom inner diameter. In some instances, the bottom outer diameter can be adapted to the inner volume of the sample container. In some instances, the bottom outer diameter can be adapted to the diameter of the plunging system.

In some instances, the wall thickness of the sample container can be between about 1 millimeter (mm) and about 1.5 mm. In some instances, the wall thickness of the sample container can be between about 1 mm and about 2 mm. In some instances, the wall thickness of the sample container can be about 1 mm. In some instances, the wall thickness of the sample container can be about 1.5 mm. In some instances, the wall thickness of the sample container can be about 1.1 mm. In some instances, the wall thickness of the sample container can be about 0.1, 1.0, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, or about 10 mm.

In some instances, the height of the sample container can be between about 50 mm and about 200 mm. In some instances, the height of the sample container can be about 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, or about 300 mm. In some instances, the height of the sample container can be about 50 mm. In some instances, the height of the sample container can be about 100 mm. In some instances, the height of the sample container can be about 150 mm. In some instances, the height of the sample container can be about 200 mm.

Figure 6:
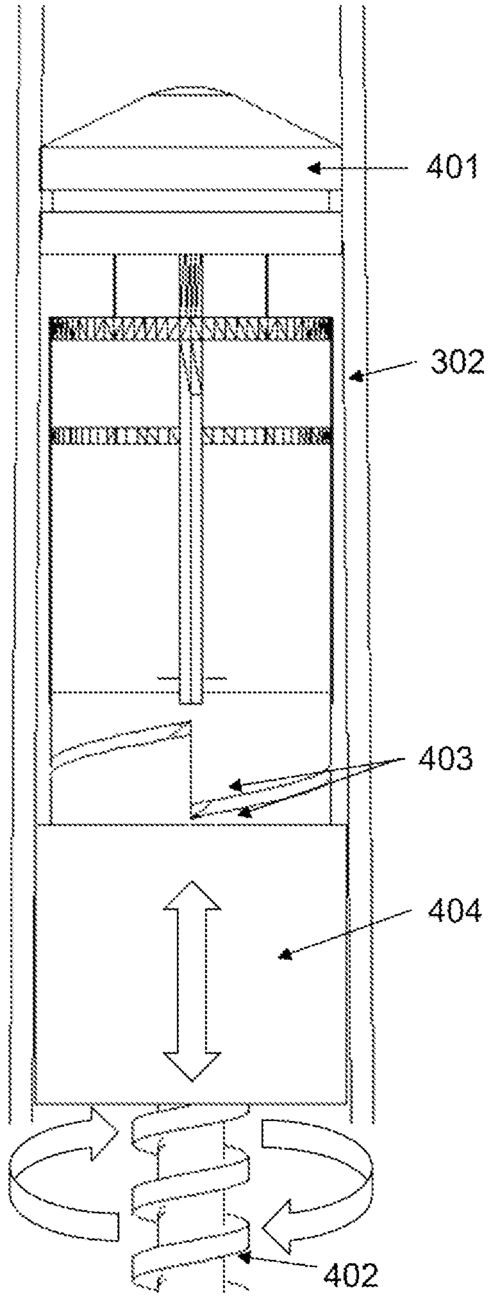
FIG. 6 illustrates one embodiment of the plunging system of the apparatus.

FIG. 6 shows the plunger, 401, can fit inside the sample container, adjacent to an adapter joint, 403. The adapter joint can be adjacent to the plunger on one side and adjacent to the plunger engagement adapter, 404, on the other side. The plunger engagement adapter 404 can engage the drive screw, 402.

Figure 7:
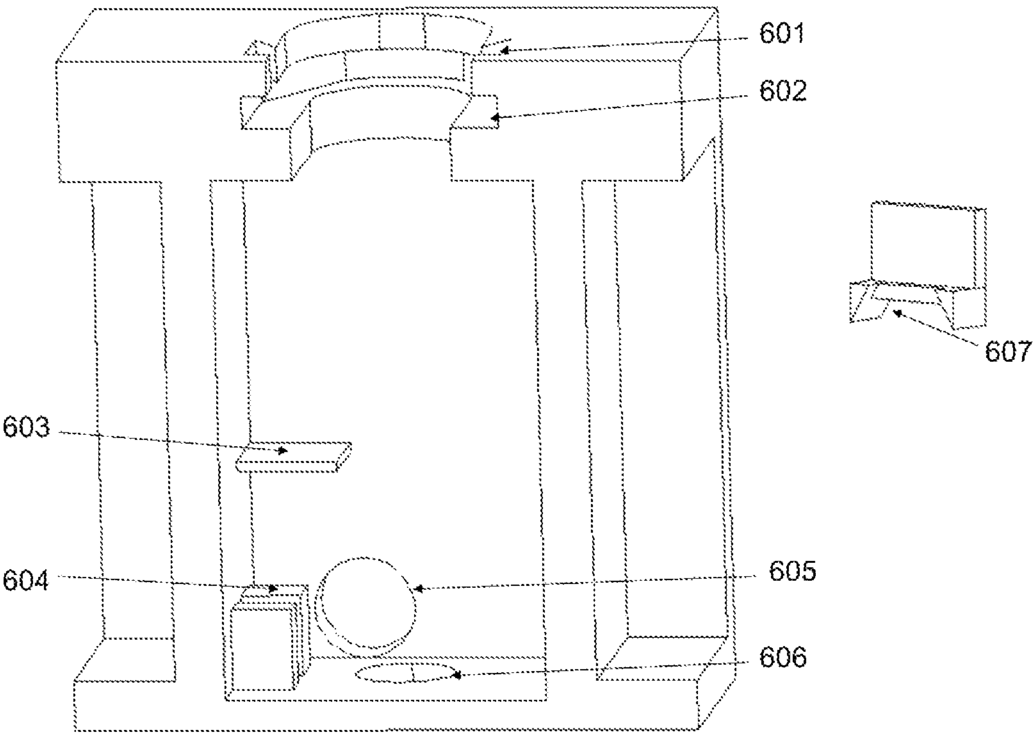
FIG. 7 illustrates one embodiment of the container mount of the apparatus.

FIG. 7 shows the container mount, 600. The container mount can comprise a locking flange slot, 601, and a flange slot, 602. The bottom flange 308 of the sample container can be inserted into the flange slot, 602, and moved into the locking flange slot, 601, to secure the sample container to the container mount by the locking flange, 607. The container mount can comprise a lower sensor depressor, 603. The container mount can comprise a lower sensor mount, 604. The container mount can comprise a wire port, 605. The container mount can comprise a screw port, 606. In some instances, the container mount can be metal. In some instances, the container mount can be non-metal. In some instances, the container mount can be plastic. In some instances, the container mount can be fabricated by 3D printing.

Figure 8:
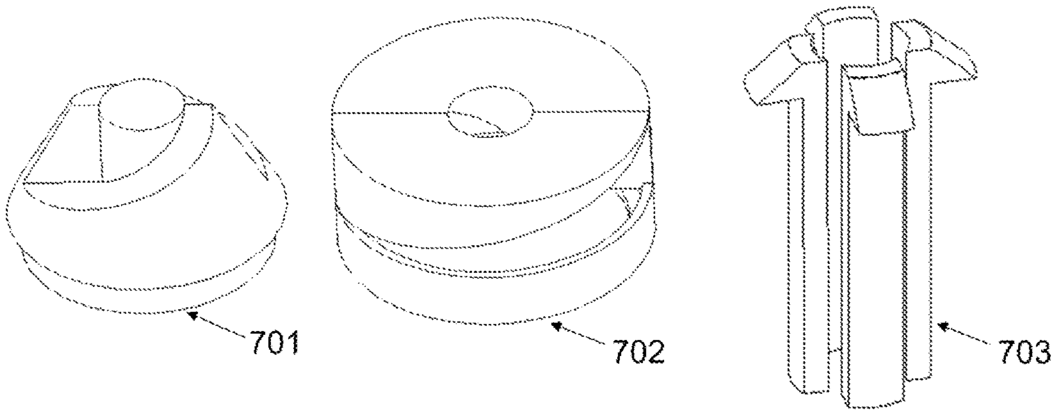
FIG. 8 illustrates three embodiments of the plunger engagement joint.

FIG. 8 shows three different plunger engagement joints, an adapter-side plunger engagement joint, 701, a plunger-side plunger engagement joint, 702, and a plunger engagement joint, 703. In some instances, the plunger engagement joint can be metal. In some instances, the plunger engagement joint can be non-metal. In some instances, the plunger engagement joint can be plastic. In some instances, the plunger engagement joint can be fabricated by 3D printing.

Figure 9:
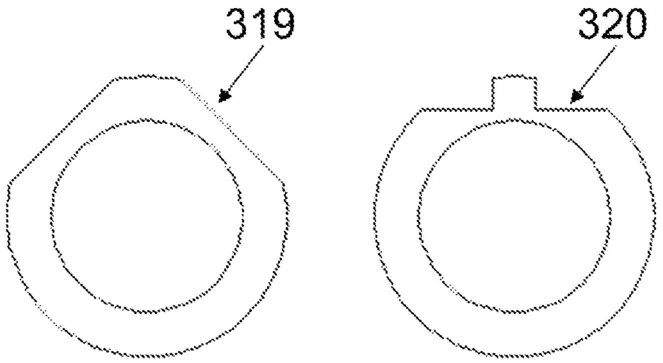
FIG. 9 illustrates two embodiments of the alignment flange.

FIG. 9 shows two different alignment flanges, 319 and 320. In some instances, the alignment flange can be metal. In some instances, the alignment flange can be non-metal. In some instances, the alignment flange can be plastic. In some instances, the alignment flange can be fabricated by 3D printing. In some instances, the alignment flange can be the bottom flange.

In some instances, the plunging system can be manually operated by a user. In some instances, the plunging system can be mechanically driven by a user. In some instances, the plunging system can be automated. In some instances, the plunging system can be computerized. In some instances, the plunging system can be automated and operated remotely by a microprocessor. In some instances, the plunging system can be a geared plunging system. In some instances, the plunger system can move the biological agents adjacent to microbubbles to the tapered end of the sample container for collection at the tip. In some instances, the plunger system can move the biological agents adjacent to microbubbles to the tapered end of the sample container such that droplets form at the tip of the tapered end.

Figure 16:
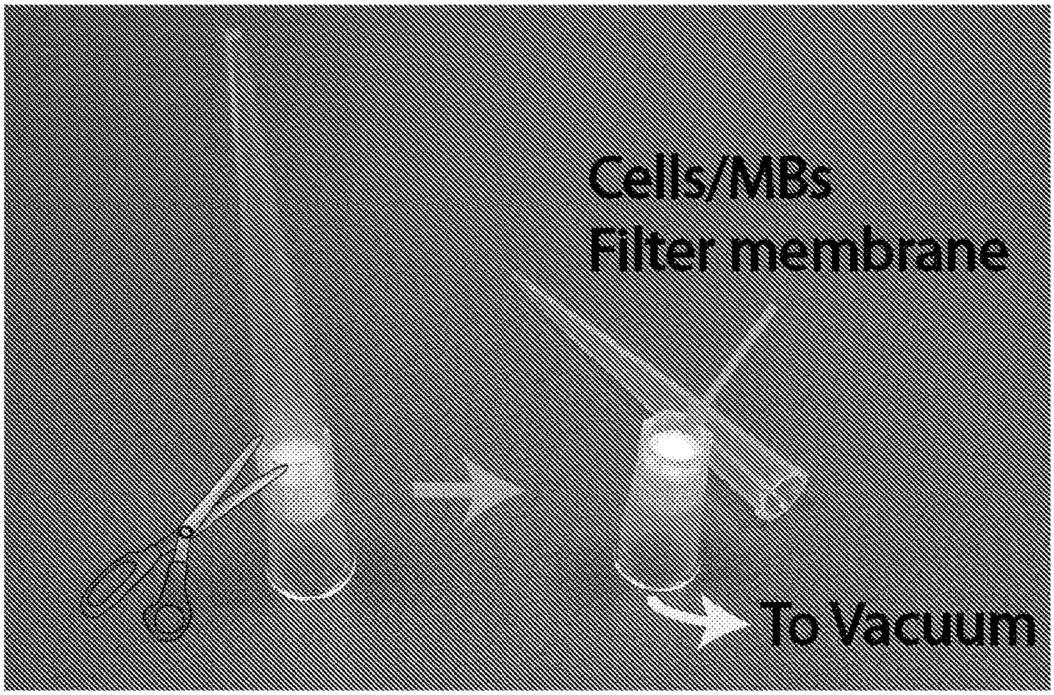
FIG. 16 illustrates one embodiment of a vacuum system of the apparatus.
Figure 17:
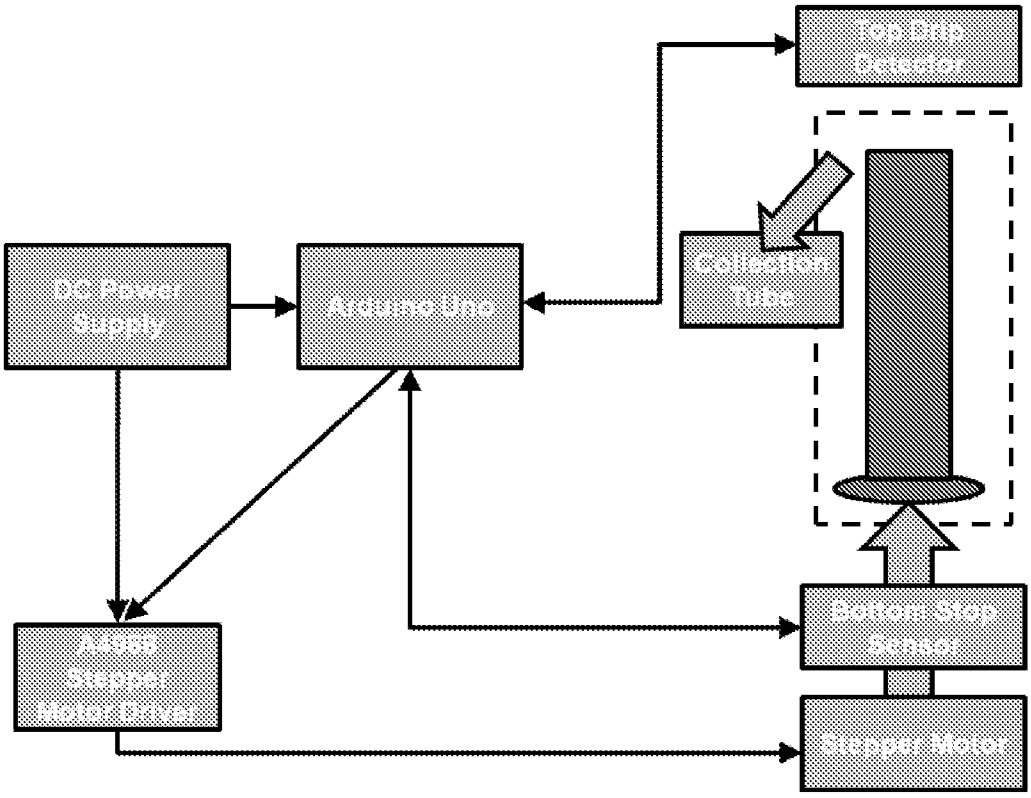
FIG. 17 illustrates an automated apparatus.

In some instances, the apparatus can comprise a vacuum system. In some instances, the vacuum system can pull the biological agents adjacent to microbubbles to the tapered end by applying a vacuum. In some instances, a filter can be inserted to the apparatus for collection of biological agents and microbubbles adjacent thereto during application of a vacuum. In some instances, a standard filter pipette tip can be modified to act as a filter membrane for collection of cells and microbubbles during application of a vacuum, FIG. 16. In some instances, a custom filter system can be constructed.

In some instances, the apparatus can comprise a collection container. In some instances, the apparatus does not comprise a collection container. In some instances, when the tapered end angle is acute, microbubbles collect into a targeted region of the collection container. In some instances, the collection container can be modified for biological agent assays, such as cell staining, molecular analysis, or cell culture, or combinations thereof, or others.

In some instances, the apparatus or parts thereof can be fabricated using 3D printing technology. In some instances, the apparatus can be operated manually by a user. In some instances, the apparatus can be automated. In some instances, the apparatus can be operated remotely by a microprocessor. In some instances, the apparatus can be an open system. In some instances, the apparatus can be a closed system. A closed system apparatus can maintain sterility. A closed system can minimize user manipulation of the apparatus. A closed system can be automated. A closed system can be automated to maintain sterility of the contents, such as the sample and microbubbles. An open system can be sterilized. An open system can be automated.

In some instances, the apparatus further comprises a collection container that has an opening at the lowest point for the final sample collection using a special container, dependent on the downstream applications, attached to the apparatus. In some instances, the collection container can be modified for downstream applications, including cell staining, molecular analysis, or cell culture, or combinations thereof. In some instances, the collection container can collect droplets of a liquid comprising one or more biological agent adjacent thereto one or more microbubbles. In some instances, the tapered end of the sample container comprises a flat tip, FIG. 11, rather than an angled tip, FIG. 10. In some instances, droplets that fall from the flat tip can fall at any direction. In some instances, droplets that fall from the flat tip can fall to any part of the stand.

Figure 11:
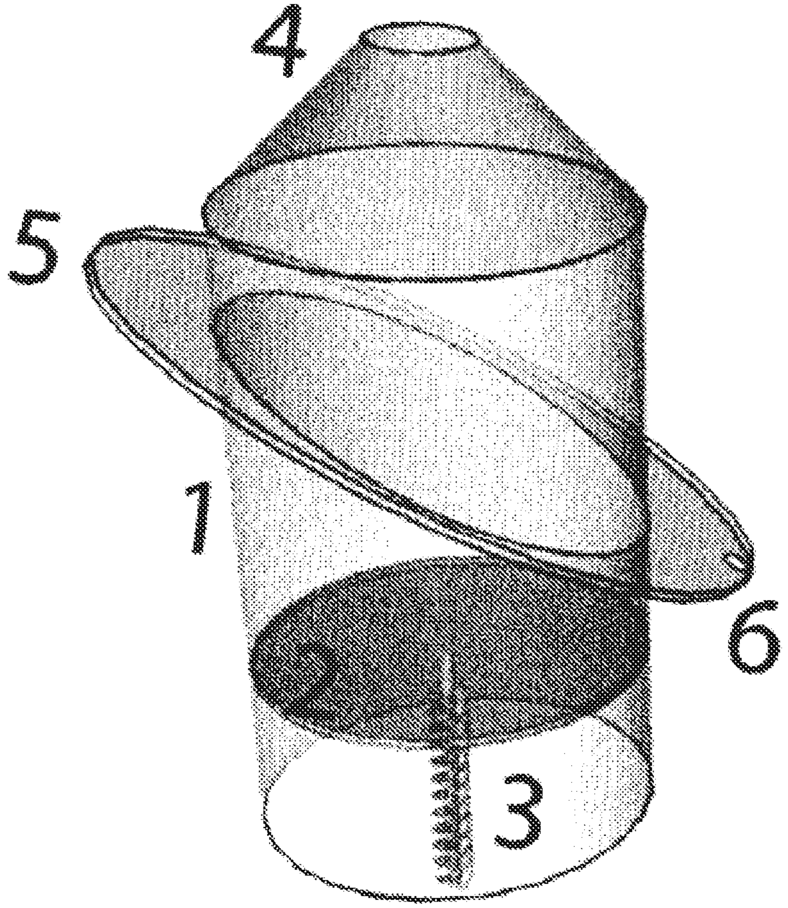
FIG. 11 illustrates a flat tip of the tapered end of a sample container.

In some instances, the tapered end of the sample container comprises a flat tip, FIG. 11. In some instances, the apparatus does not comprise a collection container. In some instances, the outer surface area of the sample container can be coated with one or more hydrophobic materials. In some instances, the inner surface area of the sample container can be coated with one or more hydrophilic materials.

In some instances, an open system apparatus can isolate biological agents from a sample. For example, this system can isolate or enrich cells harvested from umbilical cord blood and other body fluid. In some instances, the open system apparatus can isolate CTC's, bone marrow cells, stem cells, immune cells, infectious agents, or fetal cells from mother's blood. In some instances, an open system can comprise one or more plunging systems, one or more collection container systems, one or more hydrophobic outer coatings, one or more hydrophilic or blocking agent inner coatings, one or more solutions causing the biological agents to float, or combinations thereof. In some instances, an open system, when enclosed, can maintain sterility of the biological agents enriched or isolated from a sample.

In some instances, an open system apparatus of the present disclosure can comprise a collection container attached to the sample container. The collection container can collect droplets formed at the tip of the tapered end comprising the isolated or enriched biological agents with microbubbles adjacent thereto, a liquid, or combinations thereof. In some instances, the collection container can be modified for downstream applications, including cell staining, molecular analysis, or cell culture, or combinations thereof. In some instances, the tip of the tapered end of the sample container can form an acute angle relative to the horizontal axis of the sample container. In such instances, the droplets that form and fall from the angled tip, fall into a targeted section of the collection container. In some instances, the angled tip, FIG. 10, can be used for optimizing the direction of falling droplets.

Figure 12:
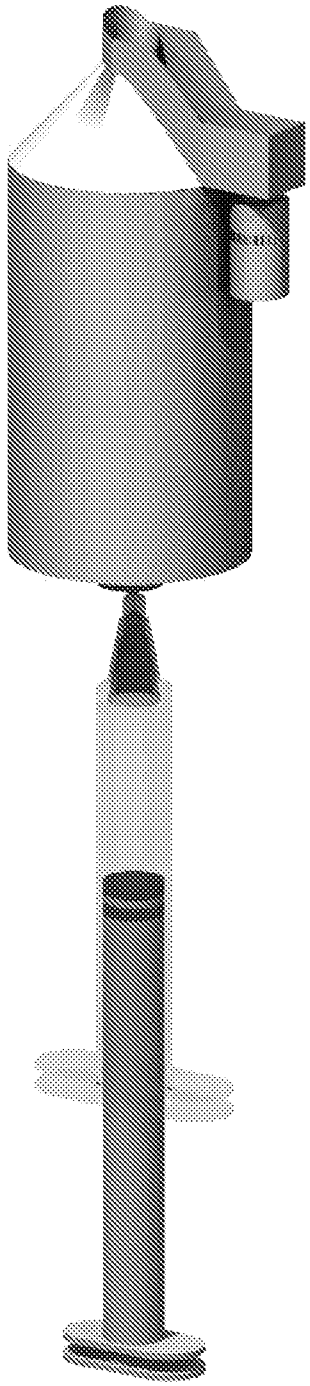
FIG. 12 illustrates a closed system apparatus of the present disclosure.

FIG. 12 illustrates a closed system apparatus of the present disclosure. In some instances, this apparatus can comprise a sterile sample container with an open end and a tapered end. In some instances, an inner surface area of the sample container can be coated with a hydrophilic material, a hydrophobic material, or combinations thereof. In some instances, a closed system apparatus can further comprise one or more collection containers. In some instances, a closed system apparatus can further comprise a needle and syringe system at the open end of the sample container wherein one or more biological agents, one or more microbubbles, or a liquid, or combinations thereof can be added to the inner volume of the sample container. In some instances, samples comprising biological agents can be added to the sample container through a sterile syringe and needle from the open end of the sample container. In some instances, the same sterile syringe and needle can be used to inject a liquid to cause microbubbles with biological agents adjacent thereto to float. In some instances, floating microbubbles with biological agents adjacent thereto can reach the tapered end after the incubation period. In some instances, a different sterile syringe and needle can be used to inject the liquid, such as to cause the agents and microbubbles adjacent thereto to reach the tapered end without a plunger system. In some instances, a needle and syringe system for injecting a liquid can be replaced with a generic intravenous fluid delivery tubing system. In some instances, the closed system apparatus further comprises blocking agents or hydrophobic materials, collection containers, or combinations thereof. In some instances, a closed system apparatus does not comprise one or more plunging systems. In some instances, a closed system apparatus can be substantially the same as an open system apparatus. In some instances, a closed system apparatus can differ from an open system apparatus in that the closed system apparatus comprises a plunging system at the open end of the sample container and the open system apparatus comprises a needle and syringe system at the open end of the sample container.

Figure 13:
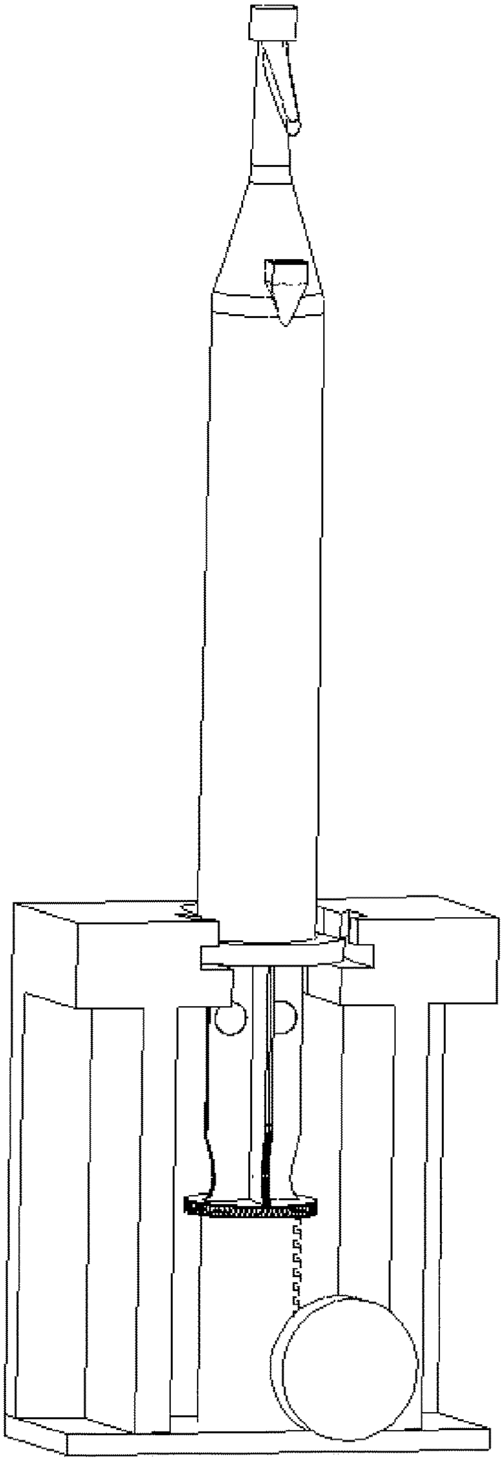
FIG. 13 illustrates an open system apparatus of the present disclosure with a manual plunger control knob.

FIG. 13 illustrates an open system apparatus of the present disclosure. In some instances, the apparatus comprise a sterile sample container with a flat tip FIG. 11, on the tapered end of the sample container. In some instances, the sample container can be placed atop a mounting base or container mount. Biological agents with microbubbles adjacent thereto can be moved towards the tapered end of the sample container using a plunging system, such as a geared plunger. In some instances, a removable harvesting cap assembly can be adjacent to the tapered end of the sample container and the biological agents isolated or enriched can be collected into the removable harvesting cap.

Figure 14:
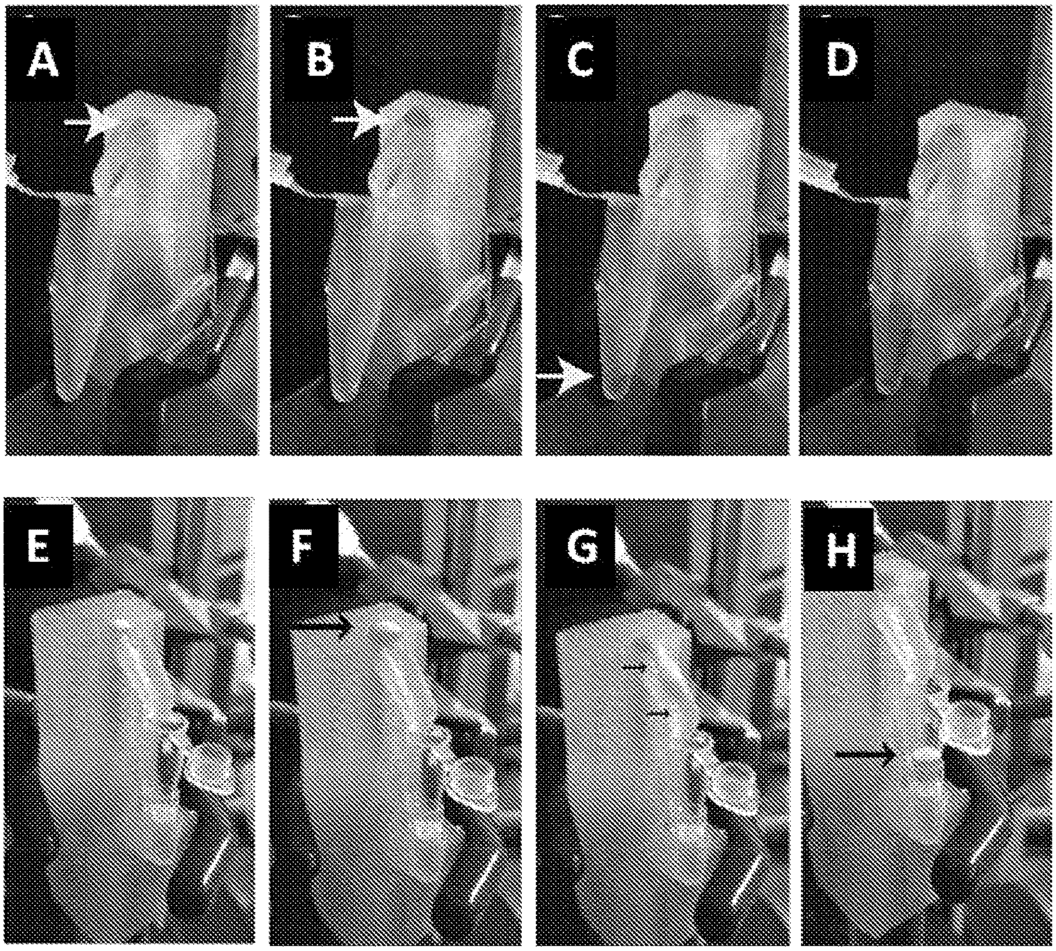
FIG. 14A-H illustrates use of the open system apparatus for isolating microbubbles

FIG. 14A-F illustrates use of the open system apparatus for isolating microbubbles from cord blood by adding a liquid comprising microbubbles to the sample container. The illustrated apparatus comprises a sterile, sample container, coated inside with non-specific interaction blocking agents and outside with hydrophobic material, a tapered end with angled tip and a collection container. FIG. 14A-D illustrates that the acute angle of the tip of the tapered end can cause each droplet that forms at the tip to fall in a single direction. FIG. 14E-F illustrates aggregation of microbubbles within the top portion of the beaded droplet that forms at the angled tip of the tapered end. Microbubbles within the top portion of the beaded droplet can stay on the top surface of the droplet as the droplet falls into the collection tube.

In some instances, the apparatus can be configured so that the tapered end can be facing ground and the agents with microbubbles adjacent thereto rise to the plunger insert at the open end. In such instances, the liquid from the inner volume of the sample container can exit through the tapered end as the plunger can be moved from the open end towards the tapered end, as the agents with microbubbles adjacent thereto continue to aggregate along the plunger. Additional liquid can be draw into the tapered end of the sample container for washing, staining, introducing nutrients or others. Purging the liquid from the tapered end and drawing additional liquid into the tapered end can be repeated one or more times. In some instances, following washing, the apparatus can be reoriented with the tapered end facing away from ground so that the agents adjacent thereto microbubbles can be collected from the droplets that can form on the tip of the tapered end.

In some instances, the tapered end of the sample container can be inverted away from ground. In this instance, biological agents adjacent thereto microbubbles can rise away from ground towards the tapered end of the sample container. In this instance, when a plunger from the open end can be moved towards the tapered end, biological agents adjacent thereto microbubbles can pass through the tip of the tapered end and collect in the first of one or more droplets that are formed.

Figure 15:
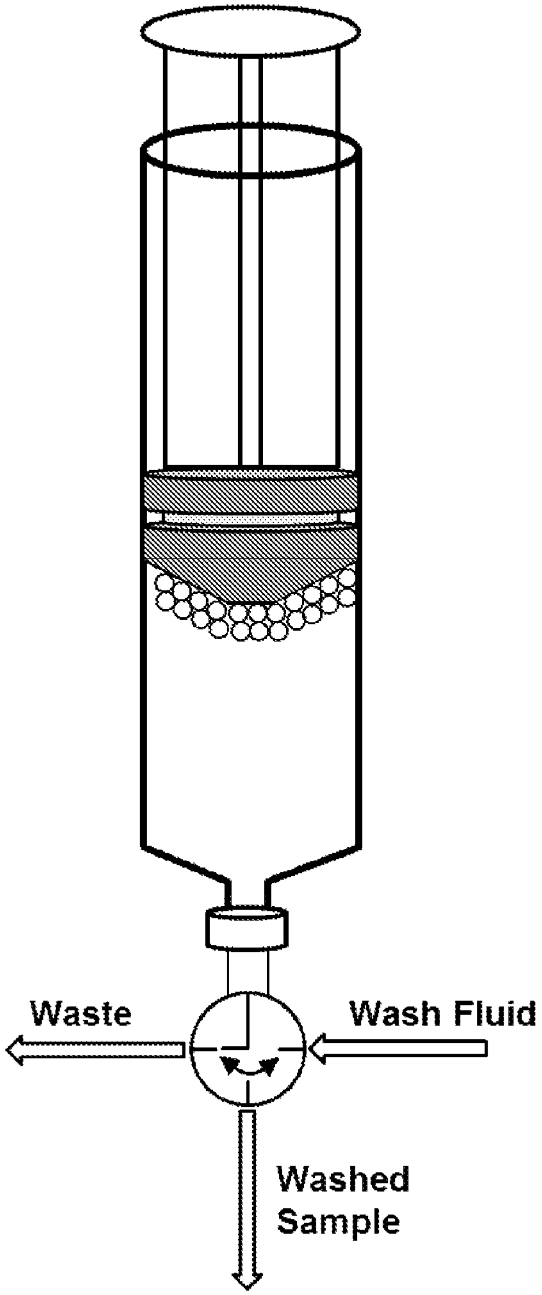
FIG. 15 illustrates one embodiment of the sample container of the apparatus.

In other instances, the tapered end of the sample container can be pointed towards the ground, with the open end inverted away from ground, FIG. 15. In this instance, biological agents adjacent thereto microbubbles can rise away from the tapered end and towards the plunger inserted into the open end of the sample container. In this instance, when the plunger from the open end can be moved towards the tapered end, liquid from the inner volume of the sample container can pass through the tip of the tapered end first. In this instance, the tapered end can also comprise a multi-valve at the tip of the tapered end. In this instance, the multi-valve can permit excess liquid to leave the sample container. In this instance, the multi-valve can permit additional liquid or wash fluid to enter the multi-valve. In this instance, the biological agents adjacent thereto microbubbles can exit the tip of the tapered end after the bulk of the liquid and can be further washed with additional liquid or wash fluid in the multi-valve. In some instances, the multi-valve can be a microfluidic component.

In some instances, the apparatus can be automated. An automated apparatus can comprise a sample container, a plunging system, one or more collection tubes, one or more sensors, one or more motors, a motor driver, a top drip detector, a power supply, a microcontroller board, or others, or combinations thereof. In some instances, the one or more sensors can be a bottom sensor (i.e. bottom stop sensor), a top detector (i.e. top drip detector), or combinations thereof. In some instances, the one or more motors can be a stepper motor. In some instances, the motor driver can be a stepper motor driver. In some instances, the power supply can be a DC power supply. In some instances, the power supply can provide power to a microcontroller board, a motor driver, or combinations thereof. In some instances, the microcontroller board can control the motor driver. In some instances, the microcontroller can control the motor driver based on feedback from the one or more detectors. In some instances, the motor driver drives the motor to move the plunger system. In some instances, the motor moves the plunger system incrementally, continuously, or in a step-wise. In some instances, the top drip detector can detect when a droplet is formed at the tip of the tapered end of the sample container. In some instances, the bottom stop sensor can detect when the plunging system cannot move further based on physical constraints of the sample container.

In some instances, the apparatus can be utilized in a laboratory or clinical setting. In some instances, the apparatus can be utilized in a non-laboratory setting. In some instances, the apparatus can be utilized in a home or residential setting. In some instances, the apparatus can be utilized in remote geographical areas. In some instances, the apparatus can be utilized in impoverished or low-income areas. In some instances, the apparatus can be utilized in the absence of sterilization equipment or centrifugation equipment. In some instances, the apparatus can be utilized for personal use. In some instances, the user can be a clinician or researcher. In some instances, the user can be a lay person. In some instances, the user can be a consumer. In one example, hematopoietic stem cells can be isolated from umbilical cord blood following a live birth using the apparatus, methods, and kits disclosed herein. In one example, immune cells can be isolated from for immunotherapy or cancer therapy using the apparatus, methods, and kits disclosed herein. In some instances, the apparatus can be utilized for blood cord banking.

In some instances, a kit can comprise one or more sample containers, one or more apparatus enclosures, one or more container mounts, one or more selection markers, components to form microbubbles, instructions for forming microbubbles and using the sample container. In some instances, a kit can comprise one or more sample containers, one or more apparatus enclosures, one or more container mounts, microbubbles with one or more selection markers adjacent thereto, and instructions for using the sample container. In some instances, a kit can comprise one or more sample container and instructions for using the sample container. In some instances, a kit can comprise one or more sample containers, one or more selection markers, components to form microbubbles, instructions for forming microbubbles and using the sample container.

What is claimed is:

1. A kit for isolation or enrichment of biological agents from a sample comprising:

a sample comprising a plurality of microbubbles in an inner volume of a sample container; and the sample container comprising:

a) the inner volume;

b) a tapered end and an open end;

c) a tip protruding from an apex of said tapered end, an end of said tip forming an acute angle relative to a horizontal axis of said sample container, and d) a plunger inserted into said open end;

wherein when the sample comprising the plurality of microbubbles is added to the inner volume of said sample container at least one microbubble of said plurality of microbubbles floats one or more biological agents of said sample, and wherein when said plunger moves towards said tip, said one or more biological agents in the at least one microbubble form isolated or enriched droplets in said tip.

2. The kit of claim 1, wherein said acute angle is between about 5 degrees and about 40 degrees.

3. The kit of claim 1, further comprising a container spout to directionally orient one or more droplets that form from said tip, wherein a droplet of the one or more droplets comprises at least a portion of said one or more biological agents.

4. The kit of claim 1, further comprising a drive screw mechanically coupled to said plunger, wherein rotation of said drive screw is mechanically converted to linear translation of said plunger, and further comprising a container mount to house a drive screw, wherein said container mount comprises a sensor depressor and a sensor mount.

5. The kit of claim 4, wherein said drive screw is operable (a) manually by a user; (b) automatically by a drive motor; or (c) automatically by a drive motor remotely controlled by a microprocessor.

6. The kit of claim 4, further comprising a plunger adapter joint and a plunger engagement adapter, wherein said plunger adapter joint is adjacent to said plunger and said plunger engagement adapter, and said plunger engagement adapter is adjacent to said plunger adapter joint and said drive screw.

7. The kit of claim 1, wherein said sample container holds (a) a sample volume of between about 1 milliliter (mL) and about 10 mL; (b) a sample volume of between about 10 mL and about 50 mL; or (c) a sample volume of between about 50 mL and about 200 mL.

8. An apparatus for isolation or enrichment of biological agents from a sample comprising: a sample container comprising:

(a) an inner volume;

(b) a tapered end and an open end;

(c) a directionally oriented container spout projecting from an apex of the tapered end at an acute angle relative to a horizontal axis of said sample container, the spout further comprising a tip, the tip also forming an acute angle relative to the horizontal axis of said sample container; and d) a plunger inserted into said open end;

wherein the acute angle of the tip can be;

the same as the acute angle of the container spout, can be different than the acute angle of the container spout, or can be more acute than the acute angle of the container spout;

wherein when a sample comprising a plurality of microbubbles is added to said sample container, at least one microbubble of said plurality of microbubbles floats one or more biological agents of said sample, and wherein when said plunger is towards said tapered end, said plurality of microbubbles collect in the directionally oriented container spout, and said one or more biological agents from said sample are isolated or enriched to form one or more droplets at said tip.

9. The apparatus of claim 8, further comprising a drive screw mechanically coupled to said plunger, wherein rotation of said drive screw is mechanically converted to linear translation of said plunger, and a container mount to house a drive screw, wherein said container mount comprises a sensor depressor and a sensor mount.

10. The apparatus of claim 9, wherein a bottom flange of said sample container is secured to said container mount by inserting said bottom flange into a locking flange slot on said container mount.

11. The apparatus of claim 9, wherein said container mount further comprises a sensor depressor and a sensor mount.

12. The apparatus of claim 9, wherein said drive screw is operable (a) manually by a user; (b) automatically by a drive motor; or (c) automatically by a drive motor remotely controlled by a microprocessor.

13. The apparatus of claim 8, further comprising a collection container to collect the one or more isolated or enriched droplets.

14. The apparatus of claim 13, wherein the collection container is adjacent to the outer surface of the sample container.

15. The apparatus of claim 13, wherein the collection container is mounted onto the outer surface of the sample container close to the tip of the directionally oriented container spout.

16. The apparatus of claim 13, wherein the collection container is modified for biological agent assays, such as:

cell staining;

molecular analysis;

cell culture; or combinations thereof.

17. The apparatus of claim 8, further comprising said sample comprising said plurality of microbubbles in said sample container.

* * * * *